(12) United States Patent
Wei

(10) Patent No.: US 12,029,743 B2
(45) Date of Patent: *Jul. 9, 2024

(54) DI-ISOPROPYL-PHOSPHINOYL-ALKANES AS TOPICAL AGENTS FOR THE TREATMENT OF SENSORY DISCOMFORT

(71) Applicant: IVIEW THERAPEUTICS, INC., Doylestown, PA (US)

(72) Inventor: Edward T. Wei, Berkeley, CA (US)

(*) Notice: Subject to any disclaimer, the term of this patent is extended or adjusted under 35 U.S.C. 154(b) by 692 days.

This patent is subject to a terminal disclaimer.

(21) Appl. No.: 16/350,559

(22) Filed: Nov. 30, 2018

(65) Prior Publication Data
US 2019/0105335 A1 Apr. 11, 2019

Related U.S. Application Data

(63) Continuation-in-part of application No. 14/544,355, filed on Dec. 29, 2014, now Pat. No. 10,195,217.

(51) Int. Cl.
*A61K 31/66* (2006.01)
*A61K 9/00* (2006.01)
*A61K 9/06* (2006.01)
*A61K 9/08* (2006.01)
*A61K 9/12* (2006.01)
*A61K 47/10* (2017.01)
*A61P 17/00* (2006.01)
*A61P 17/04* (2006.01)

(52) U.S. Cl.
CPC ............ *A61K 31/66* (2013.01); *A61K 9/0014* (2013.01); *A61K 9/0053* (2013.01); *A61K 9/06* (2013.01); *A61K 9/08* (2013.01); *A61K 9/12* (2013.01); *A61K 47/10* (2013.01); *A61P 17/04* (2018.01)

(58) Field of Classification Search
CPC ............ A61K 31/66; A61P 17/04; A61P 17/00
See application file for complete search history.

(56) References Cited

U.S. PATENT DOCUMENTS

| 4,070,496 A | * | 1/1978 | Rowsell | ................ | A23L 27/202 424/602 |
| 2015/0164924 A1 | * | 6/2015 | Wei | .......................... | A61P 3/02 424/443 |

OTHER PUBLICATIONS

Yosipovitch, Gil, et al. "Clinical characteristics of pruritus in chronic idiopathic urticaria." British Journal of Dermatology 147.1 (2002): 32-36.*

* cited by examiner

*Primary Examiner* — Bethany P Barham
*Assistant Examiner* — Peter Anthopolos

(57) ABSTRACT

The present discovery pertains generally to the field of therapeutic compounds. More specifically the present discovery pertains to certain di-isopropyl-phosphinoyl-alkanes as described herein, DIPA-1-7, DIPA-1-8, and DIPA-1-9, collectively referred to herein as "DIPA compounds", that are useful, for example, in the treatment of dermatological disorders (e.g., diseases) including: sensory discomfort (e.g., caused by irritation, itch, or pain); a skin dysesthesia; atopic dermatitis; contact dermatitis; cholestatic itch; psoriasis; sebhorrheic dermatitis; milaria rubra; ocular pain and discomfort; heat discomfort; heat stress; flushing and/or night sweats (vasomotor symptoms); and pruritus of the elderly. The applicant has found that topical delivery of DIPA compounds to the skin alleviates skin discomfort. The present discovery pertains to pharmaceutical compositions comprising such compounds, and the use of such compounds and compositions, for example, in therapy of dermatological disorders.

11 Claims, 7 Drawing Sheets

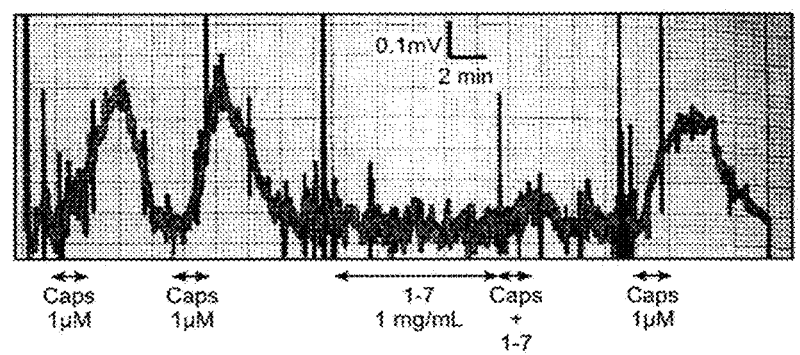
FIG. 5A  Wild Type
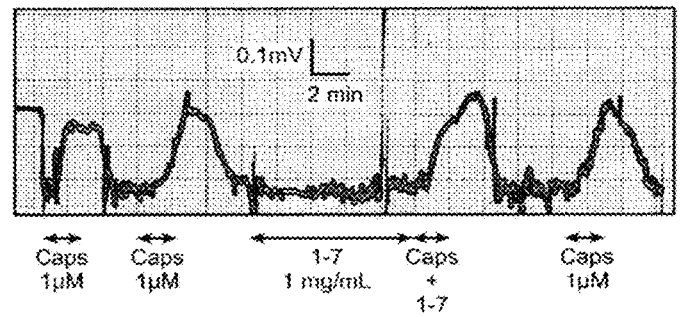
FIG. 5B  Trp-M8 KO

DI-ISOPROPYL-PHOSPHINOYL-ALKANES AS TOPICAL AGENTS FOR THE TREATMENT OF SENSORY DISCOMFORT

CROSS-REFERENCE TO RELATED APPLICATIONS

This application is a continuation-in-part of US 2015/0164924 A1, published on Jun. 18, 2015.

BACKGROUND OF THE INVENTION

1. Field of the Invention

The present discovery pertains generally to the field of therapeutic compounds. More specifically the present discovery pertains to certain di-isopropyl-phosphinoyl-alkanes as described herein (DIPA-1-5, DIPA-1-6, DIPA-1-7, DIPA-1-8, and DIPA-1-9, collectively referred to herein as "DIPA compounds") that are useful, for example, in the treatment of symptoms and disorders (e.g., diseases) of the skin. Examples of symptoms are abnormal sensations such as irritation, burning sensations, itch, or pain, collectively called a skin dysesthesia. Examples of skin disorders are acne, atopic dermatitis, prurigo nodularis, pruritus of the elderly, psoriasis, contact dermatitis, and acute and chronic urticaria. The present invention also pertains to pharmaceutical compositions comprising such compounds, and the use of such compounds and compositions, for example, in therapy.

2. Description of Related Art

Heat abstraction from the body's surfaces can refresh the senses, relieve discomfort, attenuate pain, and suppress inflammation. Abstraction of heat from body surfaces evokes sensations that are termed cool, refreshing cool, chilly, cold, icy cold and painful cold. For example, air blown onto the face from a fan or an air-conditioner can reduce tiredness and increase alertness. A wet towel applied to the forehead can relieve discomfort from a fever or a headache. The methods of heat abstraction, with gas, liquids, or solids, achieve their effects by physically lowering tissue temperatures and by activating signals to the brain.

Chemical sensory/cooling agents are molecules that can mimic the sensations of heat abstraction without a change in tissue temperatures. The exact sensations produced by chemicals depend on the selection of the active ingredient, the target site, the drug formulation, and the method of delivery. With agents currently in use, some degree of chemical cooling on the scalp and skin of the face, nostrils, and philtrum can be achieved, but the effects do not last long. For the skin of the torso and limbs overt sensations of coolness and cold are more difficult to elicit and sustain, and require high concentrations of the active agent, for example, the use of 36% l-menthol oil to treat the itch of insect bites. The skin has a keratinized layer of dead cells called the stratum corneum that acts as a formidable barrier to drug penetration into the epidermis and dermis. The neuronal receptive fields to detect temperature changes are located in the epidermal sub-layers.

The term "chemical cooling agent" can be ambiguous because, for example, chemicals such as ethyl chloride as a gas, ethanol as a liquid, liquid nitrogen, or carbon dioxide as a solid, applied to the skin can evoke heat abstraction sensations by reducing tissue temperatures. In this application, chemical cooling agents will refer only to agents that elicit sensations of heat abstraction but do not lower tissue temperatures.

The inventor has previously identified several p-menthane carboxamide compounds that, when applied to the philtrum skin, simulate effects of heat abstraction for >1.5 hr without decreasing tissue temperature (Wei, E T. Sensory/cooling agents for skin discomfort. Journal Skin Barrier Research 14: 5-12, 2012). These compounds are relatively water-insoluble.

The site where temperature is detected on the skin qualitatively affects perception of thermal comfort. Temperature sensitivity over the body surface varies over ~100 fold. The face, especially area around the eyes [periorbital] and mouth [perioral] are very sensitive, but the extremities have poor sensitivity, and the rest of the body is intermediate [Stevens et al. Temperature sensitivity of the body surface over the life span. Somatosensory Motor Research 15: 13-28, 1998]. The sensory innervation of the skin is mediated by peripheral nerves that transmit signals to the brain.

Known Phosphine Oxides

The 1-dialkyl-phosphinoyl-alkanes [e.g. total number of carbons≤16] are solvent-like molecules that require several [1 to 3] steps for synthesis. They are also known as trialkylphosphine oxides or dialkylphosphorylalkanes. Here, they are referred to as dialkyl-phosphinoyl-alkanes [DAPA]. If two of the alkyl groups are isopropyl, the DAPA is abbreviated as DIPA [di-isopropyl-phosphinoyl-alkane].

Rowsell and Spring [Phosphine oxides having a physiological cooling effect. U.S. Pat. No. 4,070,496. Jan. 24, 1978], describes a range of phosphine oxides which have a physiological cooling effect on skin and oral cavity. See, e.g., the table in columns 3 and 4 therein. Ten (10) of the compounds shown therein (Table 1) have one isopropyl group (shown as iso-$C_3H_7$). None of the compounds has two isopropyl groups.

TABLE 1

Compounds in Rowsell et al., 1978
$P(=O)R_1R_2R_3$

| # | $R_1$ | $R_2$ | $R_3$ |
|---|---|---|---|
| 2 | n-$C_7H_{15}$ | iso-$C_3H_7$ | sec-$C_4H_9$ |
| 3 | n-$C_8H_{17}$ | iso-$C_3H_7$ | sec-$C_4H_9$ |
| 7 | n-$C_6H_{13}$ | iso-$C_3H_7$ | sec-$C_4H_9$ |
| 8 | n-$C_6H_{13}$ | iso-$C_3H_7$ | cyclo-$C_5H_9$ |
| 11 | n-$C_7H_{15}$ | iso-$C_3H_7$ | cyclo-$C_5H_9$ |
| 12 | n-$C_6H_{13}$ | iso-$C_3H_7$ | iso-$C_5H_{11}$ |
| 15 | n-$C_7H_{15}$ | iso-$C_3H_7$ | iso-$C_5H_{11}$ |
| 26 | n-$C_6H_{13}$ | iso-$C_3H_7$ | n-$C_6H_{13}$ |
| 30 | n-$C_8H_{17}$ | iso-$C_3H_7$ | cyclo-$C_5H_9$ |
| 47 | iso-$C_3H_7$ | n-$C_4H_9$ | (n-$C_4H_9$)($C_2H_5$)$CHCH_2$ |

Siddall et al. [Simplified preparation of some trisubstituted phosphine oxides. J. Chemical Engineering Data 10: 303-305, 1965] reported the synthesis of 1-di-isopropyl-octane [DIPA-1-8], but Siddall et al. did not examine the bioactivity of this molecule.

BRIEF DESCRIPTION OF THE SEVERAL VIEWS OF THE DRAWINGS

FIG. 5. shows chart traces that illustrate, in the first trace (FIG. 5A "Wild Type"), the inhibition of capsaicin-induced depolarization of the isolated mouse vagus by the DIPA-1-7 embodiment, superfused at a concentration of 1 mg/mL, and, in the second trace (FIG. 5B "TRPM8 KO"), the significant absence of inhibition in the isolated TRPM8 KO (knockout) mouse vagus by DIPA-1-7, superfused at a concentration of 1 mg/mL.

BRIEF SUMMARY OF THE INVENTION

Figure 1:
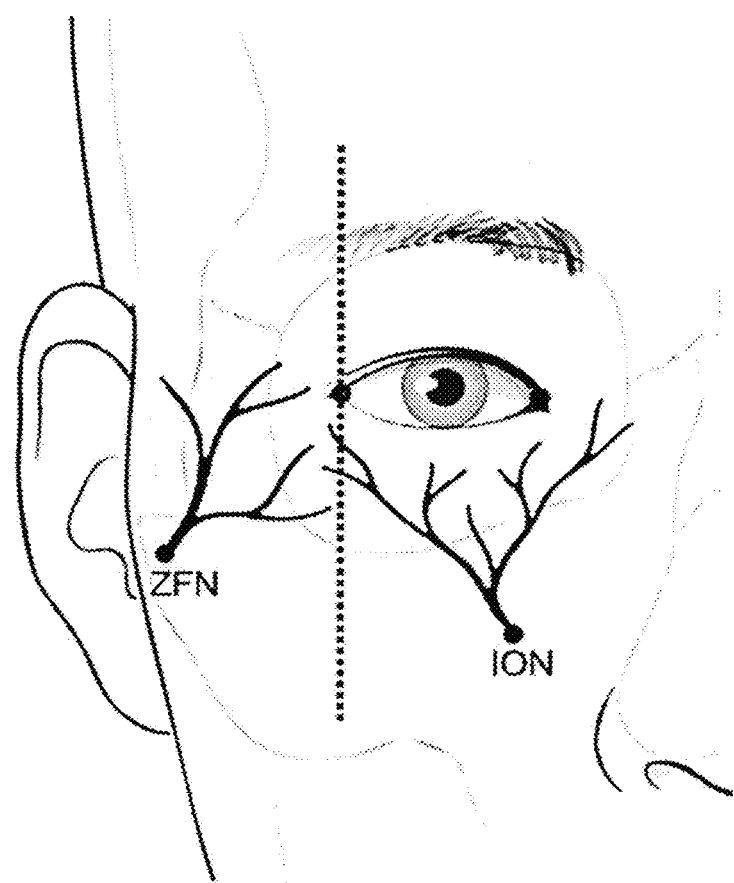
FIG. 1. is an illustration of the human face showing the innervation of the cheekbone skin by the zygomatic facial nerve (ZFN) and the infraorbital nerve (ION). The receptive fields of these nerve endings were used for testing compounds applied to the cheekbone skin. Diagram adapted from Hwang et al. [Cutaneous innervation of the lower eyelid. J. Craniofacial Surgery 19: 1675-1677, 2008].

In this discovery, it was found that structural modification of certain 1-dialkyl-phosphinoyl-alkane to the 1-di-isopropyl-phosphinoyl-alkane analog resulted in agents that will potently evoke a "dynamic cool" sensation when applied to keratinized skin. The 1-di-isopropyl-phosphinoyl-alkanes described herein are collectively referred to herein as "DIPA compounds". The skin is a frequent site of injury. Inflammation is the response of tissues to injury and the cardinal signs of inflammation are a feeling of heat [calor] at the site of injury, redness [rubor], swelling [tumor] and pain [dolor] in and around the injured tissues. The newly synthesized DIPA molecules relieve signs of skin discomfort such as irritation, burning sensations, itch, and pain from inflamed/damaged skin.

The unusual property of the DIPA molecules is water solubility and the ability to penetrate the keratinized layers of the skin [stratum corneum] to reach receptive targets underneath. The targets are located on sensory nerve endings and when activated, relieve skin dysesthesia and has a disease-modifying effect. The water solubility at therapeutically effective concentrations permits ease of formulation for delivery to target receptors.

Another aspect of the present discovery pertains to a pharmaceutical composition comprising one or more DIPA compound, as described herein, and a pharmaceutically acceptable carrier or diluent. Particularly preferred embodiments include one or more DIPA compounds and a delivery agent carrying the one or more compounds, where, the delivery agent is suitable for topical delivery. These preparations, as described herein, may be used in a method of treatment of the human or animal body by therapy, for example, for use a method of treatment of a disorder (e.g., a disease) as described herein.

DETAILED DESCRIPTION OF THE INVENTION

The present discovery relates to certain compounds (the DIPA compounds described herein) which, when delivered onto the skin, selectively and potently evoke sensations of "dynamic cool" for at least several hours. The dynamic cool can be repeated without significant diminution of the effects and can be sustained for the whole day. Thus, these compounds have applications in the treatment of skin discomfort, especially skin irritation, itch, and pain.

The structures of the preferred embodiments are shown below. The new water-soluble compounds [e.g., 1-di-isopropyl-phosphinoyl-heptane] potently [<5 mg per dose] and rapidly produce on skin robust and intense cooling sensations. This type of drug action is unusual and has not been previously recognized to be achievable on keratinized surfaces and has lead to new applications as described herein. A chemical feature, the minimum active alkyl side chain adjacent to the phosphine oxide, allows exposure of the polar phosphine oxide group to water, and increases water solubility.

Abbreviations and Terminology

DIPA compounds DIPA is the abbreviation for 1-[Diisopropyl-phosphinoyl]-alkane. The third alkyl group in the molecule may be described by a number: hence, 4, 5, 6, 7, 8, 9, and 10 correspond to the butyl, pentyl, hexyl, heptyl, octyl, nonyl, and decanyl side chain, respectively. These alkanes are linear or "normal [n]" in configuration, with the phosphinoyl group attached to the primary, or "1-" position, of the carbon chain in the third sidechain. These compounds are also known as trialkylphosphine oxides or 1-dialkylphosphorylalkanes.

TRP channels The transient receptor potential (TRP) family of cation channels are peripheral detectors of nociceptive and painful stimuli. Many of these receptors are located on the nerve membranes of sensory neurons and respond to chemical irritants and changes in local temperature by activating nerve action potentials which are the signals to be perceived and acted upon by the brain. The TRP receptors are the transducers of sensory information, and it is this transduction and effector system that regulates and protects the organism from external irritants.

Receptive field of a sensory neuron is the region in space in which a stimulus will modify the firing of the neuron. The receptive field is spatially determined by the distribution of the nerve endings of the neuron. For the epithelium, the nerve endings are interdigitated with the cell layers at the basal layer of the epithelium. A receptive field, even though smaller than a $mm^2$, when activated by the appropriate stimulus, e.g. nociceptive or pruritic, can totally dominate the attention of the brain and mind. Witness what happens when a sharp pin or sting comes into contact with skin or when a dog is pre-occupied with a flea bite.

Dermatological disorders are diseases of the skin, nails or hair. The skin has multiple keratin layers. The cornea, tongue and parts of the buccal cavity are also keratinized and thus considered as part of the skin. The body's internal surfaces, the mucous membranes, do not have a keratin layer and thereby is not considered skin. The skin is the largest organ of the body, but the epidermis is only about 1 mm thick. The epidermis is densely infiltrated with nerve endings. The epidermal turnover time, that is, the time to replace itself, is about 1.5 months.

Atopic dermatitis is an inflammatory disease of the skin. All parts of the skin may become itchy and inflamed, but the lesions are usually conspicuous on the flexures of the elbows and knees, possibly because of increased sweating in these skin areas. Many atopic dermatitis patients also have allergic rhinitis and asthma. Symptoms are more frequent in children and young adults than adults. Recently, two new medications have been approved by the US FDA for atopic dermatitis: dupilumab (a monoclonal antibody) and crisaborole (an ointment). Both medications have a slow onset of therapeutic action of >6 weeks. Dupilumab is very expensive for an one year treatment. The efficacy of crisaborole is modest and it is a greasy ointment that is not favored by atopic patients. There is room for improvement.

Urticaria also known as hives is a disease characterized by the sudden onset of "wheals" (areas of red skin, with raised and itchy bumps) on any parts of the body. The wheals can be quite large and alarming, but are not life-threatening. The triggers are usually allergy to a food item, such as seafood, but there are multiple triggers. The skin layer is intact, but it is the release of histamine from mast cells in the epidermis and dermis that is the likely cause of the wheal and itch. The condition is treatable with oral antihistamines and in more severe cases with oral prednisone, but onset of drug effect takes about 12 hours. Urticaria is a recurrent condition and in some patients may persist for more than 6 weeks (chronic urticaria). The itching skin and cosmetic disfigurement of the red wheals are annoying features of urticaria.

Itch-scratch cycle Scratching can make an itch feel better, but a vicious itch-scratch cycle can cause more damage to the skin, perpetuate inflammation, and lead to excoriations and to disfiguring lichenification. The itch-scratch cycle is a well-known phenomenon in childhood and canine atopy where shields are put up to prevent the subject from scratching at the sites of inflammation and itch. Itch prevents a good night's sleep and an atopic dermatitis patient will scratch themselves vigorously even when asleep. An effective medication should prevent itch within minutes after application and act sufficiently long to allow the subject to go to sleep. The subject should be instructed to apply the medication after washing, to use on an as-needed basis, and to apply at night before sleep, because scratching can take place after the subject is asleep. This is especially important for children. The medication should also put a break on the itch-scratch cycle.

Cholestatic Itch In certain systemic diseases, such as cholestasis, kidney dialysis procedures, and lymphoma, there are blood borne pruritogens that cause generalized itching. The exact chemical identities of these pruritogens are not well established, but are likely to be bile acids in the case of liver disease and kidney dialysis patients. The itching Is intense and causes much hardship in the patients. Sigmoid opioid antagonists, such as nalbuphine, administered orally may be effective for the itch of such patients and work by antagonizing dynorphin, an endogenous pruritogen that acts on neuronal receptors in the spinal cord.

DIPA Compounds

The DIPA compounds of the present discovery are achiral and are examples of 1-di-alkyl-phosphinoyl-alkanes [(O=)$PR_1R_2R_3$] wherein each of $R_1$, $R_2$, and $R_3$ is an alkyl group, and in particular where $R_1$ and $R_2$ are isopropyl, and $R_3$ is a linear alkyl group of 5 to 9 carbons, and which have the following general formula of Formula 1:

Formula 1

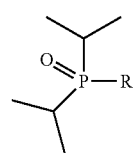

wherein R = n-pentyl, n-hexyl, n-heptyl, n-octyl, or n-nonyl

TABLE 2

DIPA compounds

| Code | Chemical Name | Formula/ Weight | Chemical Structure |
|---|---|---|---|
| DIPA-1-5 | 1-di-isopropyl-phosphinoyl-pentane | $C_{11}H_{25}OP$ 204.32 | 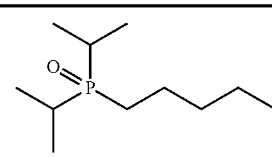 |

TABLE 2-continued

DIPA compounds

| Code | Chemical Name | Formula/Weight | Chemical Structure |
|---|---|---|---|
| DIPA-1-6 | 1-di-isopropyl-phosphinoyl-hexane | $C_{12}H_{27}OP$ 218.32 | 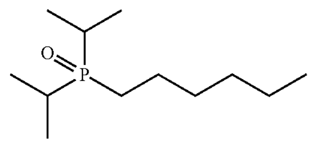 |
| DIPA-1-7 | 1-di-isopropyl-phosphinoyl-heptane | $C_{13}H_{29}OP$ 232.34 | 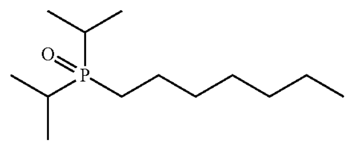 |
| DIPA-1-8 | 1-di-isopropyl phosphinoyl-octane | $C_{14}H_{31}OP$ 246.37 | 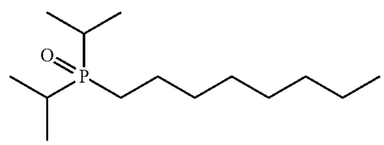 [SMILES: CCCCCCCCP(=O)(C(C)C)C(C)C] |
| DIPA-1-9 | 1-di-isopropyl phosphinoyl-nonane | $C_{15}H_{33}OP$ 260.40 | 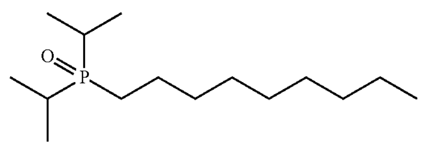 [SMILES: CCCCCCCCCP(=O)(C(C)C)C(C)C] |

Chemical Synthesis

The DIPA compounds were prepared by the following general method: 100 mL (23.7 g, ~200 mmol) of isopropylmagnesium chloride (or sec-butylmagnesium chloride in the case of the di-sec-butyl derivatives) were obtained from Acros, as a 25% solution in tetrahydrofuran (THF) and placed under nitrogen in a 500 mL flask (with a stir bar). Diethylphosphite solution in THF (from Aldrich, D99234; 8.25 g, 60.6 mmol in 50 mL) was added drop-wise. After approximately 30 minutes, the reaction mixture warmed up to boiling. The reaction mixture was stirred for an extra 30 minutes, followed by a drop-wise addition of the appropriate n-alkyl iodide solution in THF (from TCI; 60 mmol in 20 mL). The reactive mixture was then stirred overnight at room temperature. The reaction mixture was diluted with water, transferred to a separatory funnel, acidified with acetic acid (~10 mL), and extracted twice with ether. The ether layer was washed with water and evaporated (RotaVap Buchi, bath temperature 40° C.). The light brown oil was distilled under high vacuum. The final products, verified by mass as determined by mass spectrometry, were transparent liquids that were colorless. Synthesis was conducted by professional chemists at Phoenix Pharmaceuticals, Inc. (Burlingame, California), Uetikon Laboratories (Lahr, Germany) and Dong Wha Pharmaceuticals (Seoul, Korea).

Table 2 compounds are embodiments of the invention. The following compounds (Table 3) were also prepared by this general synthetic method and used for comparisons.

TABLE 3

Chemical structures of test compounds.

| Code | Chemical Name | Chemical Structure |
|---|---|---|
| 2-4 | 1-di(sec-butyl)-phosphinoyl-Butane | 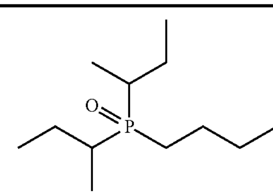 |
| 2-5 | 1-di(sec-butyl)-phosphinoyl-Pentane | 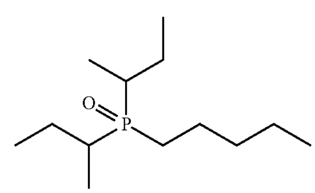 |
| 2-6 | 1-di(sec-butyl)-phosphinoyl-Hexane | 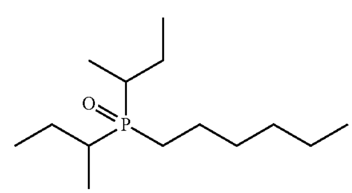 [SMILES: CCCCCCP(=O)(C(C)CC)C(C)CC] |
| 2-7 | 1-di(sec-butyl)-phosphinoyl-Heptane | 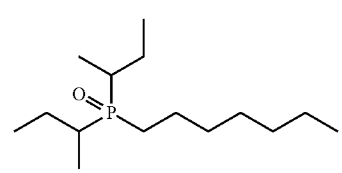 [SMILES: CCCCCCCP(=O)(C(C)CC)C(C)CC] |

TABLE 3-continued

Chemical structures of test compounds.

| Code | Chemical Name | Chemical Structure |
|---|---|---|
| 2-8 | 1-di(sec-butyl)-phosphinoyl-Octane | 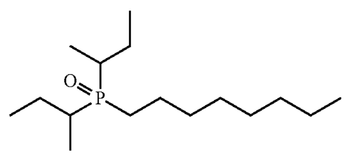 [SMILES: CCCCCCCCP(=O)(C(C)CC)C(C)CC] |
| 3-1 | 1-di(iso-butyl)-phosphinoyl-Pentane | 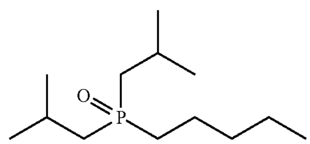 |
| 3-2 | 1-di(sec-butyl)-phosphinoyl-3-methyl-butane | 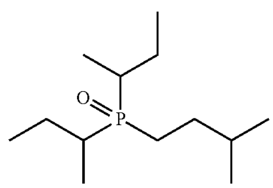 |
| 3,4-6 | 1-isopropyl-sec-butyl-phosphinoyl-hexane | 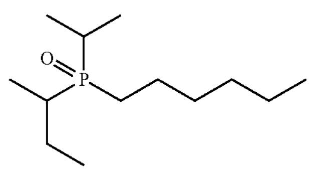 |
| 3,4-7 | 1-isopropyl-sec-butyl-phosphinoyl-heptane | 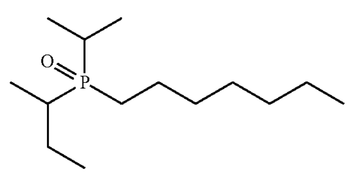 [SMILES: CCCCCCCP(=O)(C(C)C)C(C)CC] |
| 3,4-8 | 1-isopropyl-sec-butyl-phosphinoyl-octane | 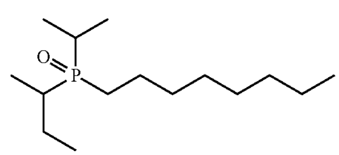 [SMILES: CCCCCCCCP(=O)(C(C)C)C(C)CC] |
| 3,4-9 | 1-isopropyl-sec-butyl-phosphinoyl-nonane | 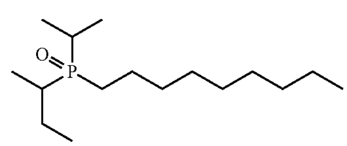 [SMILES: CCCCCCCCCP(=O)(C(C)C)C(C)CC] |

The 3,4-X series are "mixed" isopropyl-sec-butyl compounds (Table 3). These were synthesized by Dr. Jae Kyun Lim of Dong Wha Pharmaceuticals, using the method described below.

Briefly, as illustrated in the following scheme, triethyl phosphite (A) was reacted with sec-butyl magnesium bromide (B) and then hydrolysed with dilute hydrochloric acid to give the mono-alkyl compound (C). The product (C) was then reacted isopropyl magnesium bromide (D) to give the di-alkyl compound (E), which was then reacted with a suitable alkyl iodide (F) to give the target trialkyl phosphine (G).

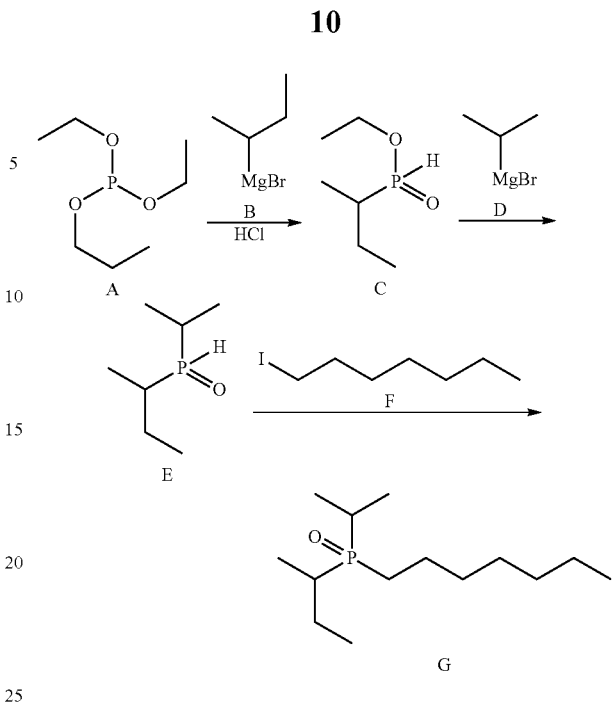

General Observations of Unusual Properties

DIPA compounds are colorless liquids with a density less than water. The preferred embodiments DIPA-1-7, DIPA-1-8 and DIPA-1-9 exert an icy sensation that can modulate skin dysesthesia caused, for example, by various dermatitis (e.g. atopic or urticarial) and on mucous membranes (esp. DIPA-1-8 and DIPA-1-9). Similar structures were described by Rowsell and Spring U.S. Pat. No. 4,070,496 (1978) ~40+ years ago but have remained dormant in the scientific literature. The '496 structures (see table) ALL have their "head" (phosphine oxide group) covered by larger, more lipophilic groups. The applicant noted that '496 did not include the di-isopropyl analogs. The applicant synthesized these analogs (which are achiral, by contrast to the structures of '496 which are >95% chiral). The applicant found that, by minimizing the two alkyl side chains to di-isopropyl, the "head" of the prototypical molecule now is more polar (hydrophilic) and more miscible in the polar environment of water. This increased water-solublility is striking (Table 4). The water solubility of the DIPA if at least 10× greater than the di-sec-butyl or the mixed isopropyl-sec-butyl analogs. The DIPA analogs are now mobile in the extracellular fluids and permeate between cells to access nerve endings in the stratum basale.

TABLE 4

Water solubility (mg/ml) of 1-dialkylphosphorylalkanes ($R_1R_2R_3P{=}O$).

| No. Carbons | 13 | | 14 | | 15 | | 16 | |
|---|---|---|---|---|---|---|---|---|
| $R_1, R_2$ | $R_3$ | | $R_3$ | | $R_3$ | | $R_3$ | |
| di-sec-butyl- | pentane | 22 | hexane | 8 | heptane | <3 | octane | <3 |
| isopropyl-sec-butyl- | hexane | 25 | heptane | 20 | octane | <3 | nonane | <3 |
| di-isopropyl- | heptane | >300 | octane | >300 | nonane | >300 | decane | <3 |

When DIPA compounds are applied to the facial skin as an aqueous solution at 1-10 mg/mL or a 1% hydrogel there is little irritation. For certain analogs, contacting the periorbital or zygomatic skin with a solution at a concentration of 1-10 mg/mL produce a sensation of "dynamic cool" that is felt within one minute after application. A single application can evoke this "energizing" sensation, which can counteract fatigue for several hours. DIPA-1-7, especially, has intense dynamic cooling.

Periorbital administration of DIPA and related di-secbutyl analogs will leave a residue on the eyelid skin. When the eyelids become wet, for example, by taking a shower or sweating, the residual compound will wash onto the cornea and cause stinging and irritation. This will limit the choice of the compound for applications wherein delivery is to the eyelid skin. Among the compounds of Formula 1, DIPA-1-8 and DIPA-1-9 have minimal residual irritation, and so are especially useful for the longer term treatment of ocular discomfort. The efficacy of DIPA-1-9 in the treatment of patients with the "dry eyes syndrome" is demonstrated in Case Study 7. DIPA-1-7 is more useful for application wherein the sensory effect is immediate and energizing.

Both DIPA-1-7 and DIPA-1-8 are useful for treatment of skin dysesthesias (e.g., skin irritation, itchy skin, or painful skin), heat discomfort, and heat stress. DIPA-1-8 is slightly longer-acting than DIPA-1-7, but is easily active across the skin, and has a lower risk for systemic absorption.

Compositions

One aspect of the present discovery pertains to a composition (e.g., a pharmaceutical composition) comprising a DIPA compound, as described herein, and a pharmaceutically acceptable carrier, diluent, or excipient. Another aspect of the present discovery pertains to a method of preparing a composition (e.g., a pharmaceutical composition) comprising mixing a DIPA compound, as described herein, and a pharmaceutically acceptable carrier, diluent, or excipient.

In one embodiment, the composition comprises the DIPA compound at a concentration of 0.005-2.0% wt/vol. In one embodiment, the composition is a liquid or semi-liquid composition (lotion, cream, or ointment), and comprises the DIPA compound at a concentration of 0.5-20 mg/mL. In one embodiment, the composition is a liquid composition, and comprises the DIPA compound at a concentration of 1-5 mg/mL. In one embodiment, the composition is a liquid composition, and comprises the DIPA compound at a concentration of 5-10 mg/mL. In one embodiment, the composition is a liquid composition, and comprises the DIPA compound at a concentration of 10-20 mg/mL.

The composition may be provided with suitable packaging and/or in a suitable container. For example, the composition may be provided as a swab, wipe, pad, or towellette (e.g., suitably sealed in a wrap) carrying a DIPA compound or a composition comprising a DIPA compound. Similarly, the composition may be provided as a patch, e.g., a controlled-release patch, e.g., suitable for application to the skin, e.g., the skin above the supraclavicular fossa or the steronomastoid muscle. Similarly, the composition may be provided as an aerosolized spray delivered from a pressurized container. Similarly, the composition may be provided in a manually-activated sprayer (e.g., with a suitable small orifice) linked to a reservoir containing a DIPA compound or a composition comprising a DIPA compound, for example, capable of delivering an unit volume (e.g., of 0.05 to 0.15 mL), for example, to the skin surface.

Use in the Manufacture of Medicaments

Another aspect of the present discovery pertains to use of a DIPA compound, as described herein, in the manufacture of a medicament, for example, for use in a method of treatment, for example, for use a method of treatment of a disorder (e.g., a disease) as described herein. In one embodiment, the medicament comprises the DIPA compound.

Methods of Treatment

Another aspect of the present discovery pertains to a method of treatment, for example, a method of treatment of a disorder (e.g., a disease) as described herein, comprising administering to a subject in need of treatment a therapeutically-effective amount of a DIPA compound, as described herein, preferably in the form of a pharmaceutical composition.

Disorders Treated

In one embodiment (e.g., of use in methods of therapy, of use in the manufacture of medicaments, of methods of treatment), the treatment is treatment of: sensory discomfort (e.g., caused by irritation, itch, or pain); a skin dysesthesia; atopic dermatitis; contact dermatitis; prurigo nodularis; urticaria; milaria rubra; lichen sclerosus atrophicus; acne; acneiform eruptions; pruritus of the elderly, pruritus from cholestasis and liver disease; pruritus from lymphoma; pruritus from kidney disease dialysis; seborrheic dermatitis; psoriasis; rosacea; ocular pain and discomfort; heat discomfort; heat stress; flushing and/or night sweats (vasomotor symptoms) in post-menopausal women; fatigue; tiredness; depression; cognitive dysfunction; and to enhance cognitive function.

The term "sensory discomfort", as used herein, relates to irritation, itch, pain, or other dysesthesias (abnormal sensations; such as burning sensations, or feeling the presence of a foreign body, or pins and needles) from the body surfaces. The term implies activation of nociceptors located on sensory nerve endings of the body. Nociceptors are stimulated, for example, by high or low temperatures, mechanical pressure, chemicals (e.g., capsaicin, acidity, pollutants, etc.), injury, inflammation, and inflammatory mediators. A DIPA compound, such as DIPA-1-8, that decreases sensory discomfort, can be termed an anti-nociceptive agent.

In one embodiment, the sensory discomfort is irritation, itch, or pain. In one embodiment, the sensory discomfort is caused by a skin dysesthesia. In one embodiment, the skin dysesthesia is skin irritation, itchy skin, or painful skin. In one embodiment, the sensory discomfort is caused by atopic dermatitis. In one embodiment, the sensory discomfort is caused by canine atopic dermatitis. In one embodiment, the treatment is treatment of a skin dysesthesia. In one embodiment, the treatment is treatment of dermatitis. In one embodiment, the treatment is treatment of atopic dermatitis. In one embodiment, the treatment is treatment of canine atopic dermatitis. In one embodiment, the treatment is treatment of contact dermatitis. In one embodiment, the treatment is treatment of urticaria. In one embodiment, the treatment is treatment of the pruritus of the elderly. In one embodiment, the treatment is treatment of the pruritus of milaria rubra. In one embodiment, the treatment is treatment of the pruritus of liver disease (cholestasis). In one embodiment, the treatment is treatment of the pruritus of patients on kidney dialysis. In one embodiment, the treatment is treatment of the pruritus of patients with lymphoma. In one embodiment, the treatment is treatment of the dysesthesia of psoriasis. In one embodiment, the treatment is treatment of the dysesthesia of neurogenic/neuropathic itch. In one embodiment, the treatment is treatment of the dysesthesia of lichen planus atrophicus. In one embodiment, the treatment is treatment of ocular discomfort. In one embodiment, the ocular discomfort is caused by eye strain; eye fatigue; eye surgery; an airborne irritant or pollutant that interacts with the eye surface; extended wear of contact lenses; excessive exposure to the sun; conjunctivitis; or the dry eyes syndrome. In one embodiment, the treatment is treatment of heat discomfort. In one embodiment, the treatment is treatment of heat discomfort for the purpose of improving athletic performance. In one embodiment, the treatment is treatment of heat stress. In one embodiment, the treatment is treatment of flushing and/or night sweats (vasomotor symptoms) in a post-menopausal woman. In one embodiment, the treatment is treatment of post-operative hypothermia or post-anaesthetic shivering. In one embodiment, the treatment is treatment is to convey a sense of refreshment to the skin in a human.

Treatment

The term "treatment," as used herein in the context of treating a disorder, pertains generally to treatment of a human or an animal (e.g., in veterinary applications), in which some desired therapeutic effect is achieved, for example, the inhibition of the progress of the disorder, and includes a reduction in the rate of progress, a halt in the rate of progress, alleviation of symptoms of the disorder, amelioration of the disorder, and cure of the disorder. Treatment as a prophylactic measure (i.e., prophylaxis) is also included. For example, use with patients who have not yet developed the disorder, but who are at risk of developing the disorder, is encompassed by the term "treatment." Treatment to enhance the basal levels of cognitive or physical performance of individuals who are considered normal or healthy is also included.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents. One aspect of the present discovery pertains to a DIPA compound as described herein, in combination with one or more (e.g., 1, 2, 3, 4, etc.) additional therapeutic agents. The particular combination would be at the discretion of the physician or the pharmacist who would select dosages using his common general knowledge and dosing regimens known to a skilled practitioner.

Examples of additional therapeutic agents include: an anti-inflammatory glucocorticosteroid; an analgesic; a sympathomimetic amine decongestant; an anti-histamine; a local anesthetic; an ophthalmic lubricant; a sunscreen ingredient; an anti-acne agent; a keratolytic agent; an anti-hemorrhoidal agent; an agent for vulvar itch or discomfort; an antibiotic; a skin moisturizer; or an anti-skin ageing agent.

Routes of Administration

The DIPA compound or pharmaceutical composition comprising the DIPA compound may suitably be administered to a subject topically, for example, as described herein.

The term "topical application", as used herein, refers to delivery onto surfaces of the body in contact with air, which includes the skin, the anogenital surfaces, the transitional epithelial surfaces of the orbit, the lips, the nose, and the anus, and the aerodigestive tract (nasal membranes, oral cavity, pharyngeal and esophageal surfaces), lower respiratory tracts, and the lumen of the gastrointestinal tract. Particularly preferred sites of application are the surfaces innervated by the trigeminal and glossopharyngeal nerves which include the scalp, facial skin, periorbital skin, lips, nasal and oral cavities, and the throat. Additional preferred sites are the surfaces of the neck, elbows and knees, which are frequently associated with the pruritus of atopic eczema and psoriasis. Yet another preferred site is the scalp, which can be a site of inflammation in psoriasis and seborrheic dermatitis.

In one embodiment (e.g., of use in methods of therapy, of use in the manufacture of medicaments, of methods of treatment), the treatment is treatment by topical administration. In one embodiment, the treatment is treatment by topical administration to skin. In one embodiment, the treatment is treatment by topical administration to facial skin. In one embodiment, the treatment is treatment by topical administration to periorbital skin, eyelid skin, zygomatic skin, malar skin, forehead skin, or scalp. In one embodiment, the treatment is treatment by topical administration to skin surface of the orbit, frontal bone, or zygomatic. In one embodiment, the treatment is treatment by topical administration to skin surface of the anus and/or the male or female genitalia. In one embodiment, the treatment is treatment by topical administration to skin above the supraclavicular fossa or the steronomastoid muscle.

The Subject/Patient

The subject/patient may be a mammal, for example, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human. In one preferred embodiment, the subject/patient is a human.

Formulations

While it is possible for a DIPA compound to be administered alone, for example, dissolved in saline or water, it may also be prepared as a pharmaceutical formulation (e.g., composition, preparation, medicament) comprising at least one DIPA compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavoring agents, and sweetening agents. The formulation may further comprise other active agents.

Thus, the present discovery further provides pharmaceutical compositions, as described above, and methods of making pharmaceutical compositions, as described above. If formulated as discrete units (e.g., swab, wipe, pads, towellettes, gels, lotion, cream, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary. Formulations may suitably be in the form of liquids, solutions (e.g., aqueous, non-aqueous), suspensions (e.g., aqueous, non-aqueous), emulsions (e.g., oil-in-water, water-in-oil); elixirs, syrups, electuaries, mouthwashes, drops, tablets (including, e.g., coated tablets), granules, powders, lozenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Additionally, the DIPA compound may be used as an adjunct in a pharmaceutical formulation or cosmetic formulation.

Dosage

It will be appreciated by one of skill in the art that appropriate dosages of the DIPA compounds, and compositions comprising the DIPA compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular DIPA compound, the route of administration, the time of administration, the duration of the treatment, other drugs, compounds, and/or materials used in combination, the severity of the disorder, and the species, sex, age, weight, condition, general health, and prior medical history of the patient. The amount of DIPA compound and route of administration will ultimately be at the discretion of the physician, pharmacist, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

Targets for Delivery

Epithelial cells line ducts, cavities and surfaces of organs throughout the body. When there are two or more layers of epithelia, it is called stratified epithelium. Historically, stratified epithelia were divided into two broad categories: keratinized stratified epithelia, and non-keratinized stratified epithelia. Keratinized epithelium, such as the epidermis of the skin, has an exterior layer of dead cells [stratum corneum] composed of keratin proteins that are tough and water-impermeable. By contrast, non-keratinizing stratified epithelia are located on "soft tissues" of the body such as the lining of the nasal and throat cavities and the oesophageal surface. Keratinizing tissues withstand injury better than non-keratinizing tissues. Non-keratinizing epithelial surfaces must be kept moist by glandular (serous and mucous) secretions in order to avoid desiccation.

The stratum corneum (keratinized layer of dead cells) is a formidable barrier to drug penetration to neuronal receptive fields embedded in epithelial tissues underneath the keratin. The barrier thickness and the layers of dead cells vary. The heel and palm have the most dead cell layers (~82 layers). The genitalia (e.g. penile shaft) and eyelids have fewer layers (4 to 8 layers). The skin of the face has about 10 to 14 layers, and the torso has about 12 to 16. The limbs have somewhat more layers (~15+). Dermatitis occurs frequently occur on the extremeties (e.g. elbow and knee flexures in atopic dermatitis) and on the trunk and scalp for psoriasis. Hand eczema frequently occurs on the hand (contact dermatitis). Urticaria can occur all over the body, the wheals appearing on the torso, neck and buttocks.

However, the stratum corneum is not a solid brick and mortar wall, but has water pores, like limestone, through which water soluble molecules may pass between cells and through cells. The intracellular water transport channels on keratinocytes are called aquaporins (Patel R et al. Aquaporins in the Skin. Adv Exp Med Biol. 2017; 969:173-191). The active ingredient must reach the nerve endings, which are located in the basal layer of the skin (stratum basale). A surprising finding here was the ability of DIPA compounds to inhibit dysesthesia when applied as a water solution on a wipe. The likely explanation is that the DIPA is passing between cells through water channels, and not across cells. The current topical antinociceptive (pain-suppressant) compounds that have efficacy on sensory discomfort of keratinized skin are high concentrations of I-menthol (36% alcoholic solution) or a local anesthetic gel. But these two types of topical medications have problems of greasy feel and irritation, and of hypersensitivity reactions.

The targets for topical delivery of the DIPA compounds are located on the nerve endings of the receptive fields of peripheral and cranial sensory nerves. For the face, the receptive fields of the ophthalmic and maxillary branches of the trigeminal nerve are the preferred target sites.

FIG. 1. is an illustration of the human face showing the innervation of the cheekbone skin by the zygomatic facial nerve (ZFN) and the infraorbital nerve (ION). The receptive fields of these nerve endings were used for testing compounds applied to the cheekbone skin. Diagram adapted from Hwang et al. [Cutaneous intervention of the lower eyelid. J. Craniofacial Surgery 19: 1675-1677, 2008].

In these studies, the primary site of testing was the zygomatic (cheekbone) skin. Alternatively, if the cooling agent is to be used for flushing and/or night sweats (vasomotor symptoms) in post-menopausal women, it may also be applied to the skin above the supraclavicular fossa or the chest. To reduce sensory discomfort on the skin, the cooling agent may be directly applied to the sites of injury and/or inflammation.

Secondary sites are the skin over the frontal bone and the scalp, but higher concentrations of cooling agent are required for these sites. In practice, the cooling agent can be sprayed or applied (e.g., with a swab or pad or within a gel, lotion, cream or ointment) over the skin of the orbit, the cheekbone (zygomatic), or on the skin beneath the eye, between the cheekbone and nose. The important receptive fields are from the sub-divisions of the trigeminal nerve, namely, the zygomaticfacial nerve of the maxillary nerve (V2) and the supraorbital and supratrochlear branches of the frontal nerve (V1).

One unusual feature of DIPA compounds is that they leave a reservoir in the skin after application, so that after the initial sensations have dissipated, the dynamic cooling sensation returns when the skin is moist again. This feature is especially beneficial for use of DIPA-1-7 and DIPA-1-8 in conditions of elevated environmental temperature. When sweating is activated by heat, the sweat re-solubilizes DIPA-1-7 and DIPA-1-8 and enhances and perpetuates the sensory effect. This self-regulating feedback mechanism makes the effect of DIPA-1-7 and DIPA-1-8 more robust, efficacious, and prolonged.

Methods of Delivery

The delivery of the DIPA compounds can be achieved with the compound dissolved in a liquid vehicle, e.g., in water or saline, or a solution, a hydrogel, a lotion, on a swab, wet wipe, or as an aerosolized mist in a solid or semi-solid vehicle, e.g., a cream or an ointment. Gels are semisolid, jelly-like formulations with varying degrees of viscosity. A gel forms a solid three-dimensional network that spans the volume of a liquid medium. Gels are made with gelling agents that cross-link or associate with a liquid phase. Examples of gelling agents are: cellulose derivatives [methylcellulose, carboxymethylcellulose, hydroxylpropylcellulose; carbomers [carbopol®910, carbopol®941]; poloxamers [Pluronic®, Tween]; carbomer polymers, and natural polymers such as tragacanth, acacia, gelatin, sodium alginate, alginic acid, and xanthan gum. A single-phase system is a gelling agent plus an active ingredient that dissolves [in water] without visible particles and looks clear. A topical gel optimally liquefies when in contact with skin or mucous membranes. The compounds of Formula 1 are attractive for delivery as gels because they dissolve in water and form a one-phase system at therapeutic concentrations. The methods for formulating topical gels are well-known to the art and extensively described in such sites in Lubrizol.com [a company that manufactures ingredients for cosmetics, personal care, skin care, and eye care].

For a solid or semi-solid vehicle, a preferred concentration of the DIPA compound is 0.01 to 2.0% wt/vol. Unless otherwise stated, wt/vol is measured in units of $g/cm^3$ or g/mL and so 0.01% wt/vol is obtained from 0.1 mg (0.0001 g) DIPA compound in 1 $cm^3$ of composition; and 2% wt/vol is obtained from 20 mg (0.02 g) DIPA compound in 1 $cm^3$ of composition.

For a liquid vehicle, a preferred delivered volume is 0.02 to 0.15 mL. Such a volume, delivered for example as a lotion or a wipe, does not cause much residual liquid at the delivery site, as the liquid is absorbed.

For a liquid vehicle, a preferred concentration of the DIPA compound is in the range of 0.5 to 30 mg/mL. For the orbit, a preferred concentration is 1 to 5 mg/mL. For the zygomatic and infraorbital skin, a preferred concentration is 5 to 10 mg/mL. For the forehead skin and scalp, a preferred concentration is 10 to 30 mg/mL.

A preferred amount of the DIPA compound delivered at the site of application is 0.01 to 5 mg; for example, 0.1 to 5 mg.

Wiping of the DIPA compound on the target skin can be done with pre-medicated wipes, which are well-known in personal care products, for example, to wipe a baby's skin after a diaper change, or to remove make-up on the face (e.g., Pond's 6"×8" (15 cm×20 cm) Clean Sweep Cleansing and Make-up Remover Towelettes). Usually, these wipes are packaged as a single-use sealed unit or in a multi-unit dispenser. For single units, suitable wrapper materials are those which are relatively vapor impermeable, to prevent drying out of the wipe, and able to form a "peelable" seal. Examples of suitable wipe materials for practicing this discovery include polyamide (20% Nylon)-polyester, rayon (70%)-polyester (30%) formed fabric, polypropylene nonwoven, polyethylene terephthalate (PET), polyester polypropylene blends, cotton, viscose, rayon, or microfibers (synthetic fibers that measure less than one denier or one decitex).

Alternatively, a solution containing a DIPA compound may be supplied in a reservoir bottle with individual applicators, or as a pre-packaged individual unit. For example, Puritan 803-PCL applicators are ideal cotton-tipped applicators attached to a 3-inch (~7.5 cm) polystyrene rod for delivery of a DIPA compound onto the periorbital skin. Examples of how such applicators can be individually packaged are the SwabDose™ from Unicep Corporation (1702 Industrial Drive, Sandpoint, Id., USA), and the Pro-Swabs from American Empire Manufacturing (3828 Hawthorne Court, Waukegan, Illinois, USA). Each applicator tip is saturated by dipping the absorbent material of the tip (e.g., 40 to 100 mg of cotton) in 0.1 to 1.5 mL of an aqueous solution of a DIPA compound and packaged in an individual container.

For application to the face, the individual is instructed to gently apply the cream, lotion, gel, or wet wipe onto, or to spray, to the target facial skin with the eyelids shut, or other skin surface(s). The instructions for application may include teaching the individual to repeat application, or "topping up", to ensure that sufficient composition is delivered to the target. Once the subject has learned what to expect, the individual can adjust the dosage (e.g., by dabbing at the medial or lateral edges of the orbit), as needed, to achieve the desired effect. It has been observed that individuals learn how to effectively apply the cooling agent after one or two trials and do so without risks of discomfort (e.g., eye discomfort).

For application to the anogenital skin or other highly sensitive surfaces, the DIPA compound may be wiped or sprayed, for example, to deliver volumes of approximately 0.15 mL per unit. Alternatively, a dropper may be used with a wipe with an ultrasoft material such as 100% viscose or cotton.

Mechanisms of Action

The peripheral sensory neurons express receptors and ion channels on their membranes and detect various stimuli. Stimuli (chemical or physical) are converted by the receptor to electrical signals which are transmitted to the central nervous system (brain) and become a sensation. These sensory receptors are transducers and the process is called transduction.

DIPA compounds applied topically relieve heat stress and skin discomfort by evoking a sense of "dynamic cool" at sites of application. The feeling is of robust freshness, as if suddenly a fresh, cool breeze was blown on the skin (e.g., on the face) or cold water was splashed onto the skin. This effect especially with DIPA-1-7 is intense. This transduction process, receptor mechanisms, and the significance of dynamic cooling for anti-fatigue, anti-heat stress, and anti-pruritic actions are further discussed herein.

Neurophysiology:

Small myelinated (Aδ) and unmyelinated fibers (C fibers) increase afferent firing rate when skin temperature is lowered, for example, between 35° C. and 15° C. These neuronal signals that detect heat abstraction are transmitted to the central nervous system and generate conscious perception of coolness and cold. When skin temperature is raised from 35° C. and 40° C., firing rates are increased in C fibers and these fibers signal warmth [Hutchinson et al. Quantitative analysis of orofacial thermoreceptive neurons in the superficial medullary dorsal horn of the rat. J. Neurophysiol. 77, 3252-66, 1997]. The receptive mechanisms and "cable lines" for cool/cold and warm are separate and distinct, but reciprocally inhibit each other in the brain and perhaps also in the periphery. The sensory receptors are modality specific and do not respond to mechanical stimulation. At the molecular level, the target binding sites for cooling agents are thought to be located on TRP ion channel receptors that depolarize in response to a drop in temperature. Heat abstraction decreases the threshold for discharge of the receptor, and the facilitated depolarization initiates the axonal responses that create the neuronal signal.

The central response of these neurons has been recorded and studied from rat superficial medullar dorsal horn that responds to innocuous thermal stimulation of the rat's face and tongue [Hutchinson et al., 1997]. Step changes of −Δ5° C. stimulated cells with both static firing rates and cells that had mainly dynamic properties [Davies et al. Sensory processing in a thermal afferent pathway. J. Neurophysiol. 53: 429-434, 1985]. Similar studies in cats and humans showed that step decreases in temperatures (dynamic changes), as low as Δ0.5° C./second, were readily detectable by neurons and by psychophysical measurements [Davies et al. Facial sensitivity to rates of temperature change: neurophysiological and psychophysical evidence from cats and humans. J. Physiol. 344: 161-175, 1983].

From a study of the spike patterns of neuronal discharge (impulses/second), it was clear that dynamic, and not static firing responses to a change in temperature were the most powerful stimuli for generating coolness/cold sensations That is, the brain "sees" −Δ° C./t and not absolute ° C. Thus, a cooling agent that simulates −Δ° C./t on nerve discharge will produce "dynamic cooling".

Relationship of Dynamic Cooling to Treatment of Skin Dysesthesia and Pruritus

Dynamic cooling (versus static cooling/cold) is essential for a robust sensory effect. For example, if one is tired and driving a vehicle, turning on the air-conditioning and blasting the air onto the face will counteract fatigue [dynamic cooling]. But just turning on the air conditioner to lower ambient temperature and being chilled inside the vehicle [static cooling] will not make much of a difference. The benefits of the topical sensory therapy are illustrated by the Case Studies described herein.

Receptor Mechanisms:

There is a general view that "TRP-" ion channel receptors (A1, M8, and V1 to 4) are the principal physiological elements for physiological temperature detection. The TRPM8 receptor is the one that responds to sensory/cooling agents such as menthol and icilin [McKemy et al. Identification of a cold receptor reveals a general role for TRP channels in thermosensation, Nature, 416, 52-58, 2002]. TRPM8 is a protein with 1104-amino acid residues and has six transmembrane domains. Activation of this receptor by lowering ambient temperature results in opening of pores of transmembrane loop and non-specific cation entry into the cell. Depolarization of TRPM8 receptors on sensory neurons may then transmit signals primarily via Aδ (and some C) fibres to the brain.

While this concept for the role of TRPM8 in sensory physiology may be valid for physical changes in temperature, the interpretation of the sensory effects of chemical agents such as menthol and icilin are more complex. Menthol not only stimulates TRPM8 in vitro, but also TRPV3, a receptor associated with warmth and glycinergic transmission [Macpherson et al. More than cool: promiscuous relationships of menthol and other sensory compounds. Mol Cell Neurosci 32:335-343, 2006: Sherkheli et al., Super-cooling agent icilin blocks a warmth-sensing ion channel TRPV3, Scientific World Journal, 2012; Cho et al. TRPA1-like channels enhance glycinergic transmission in medullary dorsal horn neurons. J Neurochem 122:691-701, 2012]. Thus, menthol and icilin are "promiscuous" cooling agents and their specific sensory effects may not be associated with any one particular receptor protein. A laboratory reagent specific and selective for TRPM8 will be valuable for experiment and is not currently available.

The Applicant has screened a large database of cooling agents but, surprisingly, only the DIPA compounds produced super-robust dynamic cooling on skin. DIPA-1-8 and DIPA-1-9 also produces strong cooling and its actions are prolonged, but it does not quite have the super "wow" cooling effects of DIPA-1-6 and DIPA-1-7. Other cooling agents are less stimulating or have shorter durations of action and thus less suitable for the uses contemplated herein. Thus, the DIPA compounds, by contrast to menthol and icilin, are ideal selective reagents on TRPM8 function.

It may be concluded that DIPA-1-7, DIPA-1-8, and DIPA-1-9 bind to a site on a voltage-gated ion channel receptor located on a nerve ending that is sensitive to a decrement in physical temperature. This event facilitates neuronal depolarization to a cooling/cold signal, and an action potential is transmitted via Aδ and C fibers towards the central nervous system. If the nerve ending is located on the facial skin, the signal is recordable from dorsal surface of the trigeminal nucleus in the brainstem. Further rostral transmission and integration of signals give rise to the perception of coolness/cold and its topographical association with the site of stimulation.

When one examines the structure-activity relationships (SAR) of the DIPA compounds, it is noted that when $R_1=R_2=$isopropyl and $R_3=C_6$ to $C_9$, then cooling is observed. Strong cooling of long duration is obtained with $R_3$=n-octyl ($C_8$). Refreshing cooling of long duration is obtained with $R_3$=n-nonyl ($C_9$). The special attribute of the n-nonyl analog is the absence of any burning/tingling sensations, even at high concentrations of 5% in water. By contrast, the sec-butyl containing analogs are much less potent. As shown in the studies described herein, this distinction between di-sec-butyl and di-iso-propyl compounds is also seen in animal studies on shaking behavior, an indicator of cooling actions in the rat (because shaking is inhibited by heat).

The shaking behavior assay is manifested as a rapid alternating contraction of the supination and pronation muscles about the spinal axis, like a wet dog, can be readily observed and counted. All fur-coated and feathered animals—when wet and cold—shake, like a wet dog [Dickerson et al., Wet mammals shake at tuned frequencies to dry. J. Royal Society, Interface 9, 3208-3218, 2012; Ortega-Jimenez, V. M. et al. Aerial shaking performance of wet Anna's hummingbirds. J. Royal Society, Interface 9, 1093-9, 2012; Wei, Pharmacological aspects of shaking behavior produced by TRH, AG-3-5, and morphine withdrawal, *Federation Proc.* 40: 1491-1496, 1981].

"Wet-dog shaking" has been studied in detail in animals. Rats can shake their head, the upper torso, or the shaking can be sufficiently violent to affect the whole body and make the animal lose its balance. DIPA-1-7 and DIPA-1-8 elicit the vigorous type of shaking. The purpose or survival value of shaking to fur-coated and feathered organisms is to remove water droplets trapped on or near the skin. Removal of the water droplets on or near the skin by shaking reduces the organism's need to expend energy to remove the water by evaporation. The likely equivalent behaviour to shaking in humans is shivering, a condition caused by generalized sensations of coolness/cold. Human subjects recovering from the deep hypothermia of anaesthesia manifest vigorous shaking; a condition called post-anaesthetic shivering. Human subjects can also do a "wet shake" by deliberate effort when coming out of a swimming pool.

Icilin (1-[2-hydroxy]-4-[3-nitrophenyl]-1,2,3,6-tetrahydropyrimidine-2-one) induces vigorous shaking in rats [Wei. Chemical stimulants of shaking behavior. J. Pharmacy and Pharmacology 28: 722-724, 1976], Surprisingly, two potent p-menthane carboxamide cooling agents [(R)-2-[((1R,2S, 5R)-2-isopropyl-5-methyl-cyclohexanecarbonyl)-amino]-propionic acid ethyl ester, and [((1R,2S,5R)-2-isopropyl-5-methyl-cyclohexanecarbonyl)-amino]-acetic acid isopropyl ester], which have $EC_{50}$ values similar to icilin at the TRPM8 receptor, do not evoke shaking (when injected at 50 mg/kg s.c. in male rats and observed for 1 hour. Icilin activation at the TRPM8 receptor is abrogated by a G805A mutation at the second to third transmembrane loop, but the effects of menthol are not affected. It is likely that DIPA-1-6, DIPA-1-7, and DIPA-1-8 also have specific sites of binding and activation on the TRPM8 receptor which are not shared by menthol or p-menthane carboxamides. Recent studies by Wei and Kuhn have shown that DIPA-1-6 and DIPA-1-7 are still active on TRPM8 receptors with the G805A mutation.

Studies by Watson et al., 1978 [New compounds with the menthol cooling effect. J. Soc. Cosmet. Chem. 29: 185-200, 1978] show that a polar oxygen moiety capable of hydrogen bonding is an essential structural requirement for bioactivity. A Hückel molecular orbital calculation (using Molecular Modelling Pro v6.0.3, ChemSW Inc, Fairfield, CA 94534, USA) on the isopropyl analogs versus the sec-butyl analogues favours a slightly higher partial negative charge (0.007 e) on the oxygen in the sec-butyl entities, suggesting that the sec-butyl substituents facilitate a higher affinity of the oxygen to the hydrogen binding site of the receptor. Thus it is possible that isopropyl, with a "looser" affinity can associate and disassociate with the receptor more rapidly, favouring the generation of a dynamic onset and offset response of the receptor. This rapid interaction with the binding site will favour a more "dynamic" and intense stimulation of cooling and give rise to the phenomenon known as shaking.

Another possibility is that DIPA-1-7 has a dual action on TRP receptors, so that it stimulates TRPM8 and, at higher concentrations, stimulates TRPV1. The dual action will give a cold-hot synergy that might lead to a more dynamic cooling sensation.

TRPM8, TRPA1, and TRPV1 Receptor Assays TRPM8 is a nonselective cation channel activated by cold temperatures and cooling compounds such as menthol and icilin. Here, the in vitro effects of test compounds were evaluated on cloned hTRPM8 channel (encoded by the human TRPM8 gene, expressed in CHO cells) using a Fluo-8 calcium kit and a Fluorescence Imaging Plate Reader (FLIPRTETRA™) instrument. To examine the specificity of the test compounds, further tests were conducted on TRPV1 channels (human TRPV1 gene expressed in HEK293 cells) and TRPA1 channels (human TRPA1 gene expressed in CHO cells). The assays were conducted by ChanTest Corporation, 14656 Neo Parkway, Cleveland, OH 44128, USA.

In a second set of experiments, cells, grown in culture, were seeded at an approximate density of 30,000 cells/well overnight, and loaded for ~1 hr with 2 M Fura-2 (Molecular Probes, Leiden, The Netherlands), and then placed on glass coverslips. Test solutions were added with a micropipette positioned close to the cells. Emission intensity from cells was measured for 90 sec, at every 4 or 5 sec, using excitation wavelengths of 340 and 380 nm and an emission of 520 nm. Fluorescence emission intensity ratios at 340 nm/380 nm excitation (R, in individual cells) were recorded with a FlexStation and the ImageMaster suite of software (PTI, South Brunswick, NJ). Samples were tested in triplicate at each concentration and the averaged values analyzed by non-linear regression using an a sigmoidal function fit of the points to obtain an estimated EC50 (median effective concentration) (GraphPad Prism software, La Jolla, Califoria).

The receptor assays in vitro provide information of relative activity, but do not yield too much information.

Selection of Active Ingredient

Ideally, an active pharmaceutical ingredient (API) formulated for delivery to the keratinized skin should be stable, non-toxic, and sufficiently long-acting and potent to activate the mechanisms that result in an anti-fatigue, anti-heat, or anti-nociceptive effect. The API should be dissolved and evenly dispersed in a composition so that during manufacture the formulation maintains a constant concentration. The final product should meet standards of cleanliness and sterility. For purposes of formulation, the API can be a liquid at standard conditions of temperature and pressure (STP) and that is evenly dissolved in aqueous solutions at neutral pH and/or isotonicity. Sterility of the final product can be optimally achieved by using purified reagents and filtration through micropore filters, heating, or irradiation. Standard excipients, such as emulsifying agents, isotonic saline, solvents, stabilizing agents, and preservatives, may be added to optimize the formulations, but the important ingredients should be preferably soluble in aqueous media such as purified water or a standard dermatological solvent.

For a given individual, the perceived sensation is a function of the particular cooling agent, the dose, the vehicle used to carry the cooling agent, the method of topical delivery, and the nature of the target surfaces. The Applicant has screened a number of candidate compounds, such as p-menthane carboxamides, on the facial skin (Wei. Sensory/ cooling agents for skin discomfort. Journal Skin Barrier Research 14: 5-12, 2012). The studies here identify DIPA compounds as having the preferred desired properties of an ideal anti-fatigue, anti-heat, and anti-nociceptive agent.

To summarize, the design concepts for the selection of DIPA compounds are:

The definition of a rationale for using a "dynamic cool" sensation on skin to relieve sensory discomfort and a description of the neurophysiology and receptor mechanisms of this action. This sensory effect in unusual and found in the DIPA compounds but not found with structurally similar compounds.

Devising a delivery method for the ideal compound which exploits the water solubility of these analogs, and reduces the need to use excipients.

Finding an ideal compound by experiment: DIPA-1-7, DIPA-1-8, and DIPA-1-9 are water soluble (a clear solution is obtained at up to 20 mg/mL in distilled water), stable to heat, and may exert a "robust cool" sensation for up to five to seven hours at an applied concentration of 1 to 10 mg/mL. Tachyphylaxis does not develop to repeat applications.

Defining the receptor targets of these compounds in vitro, and conducting experiments to show the selectivity of the chosen DIPA.

Defining an in vitro isolated nerve preparation that shows an anti-nociceptive action of DIPA-1-7 in a peripheral nerve, and showing that this effect is abrogated on the nerve from a TRPM8 knockout mouse.

Defining an animal model (of "wet-dog shakes") that will illustrate the "dynamic cool" properties and allow further study of mechanisms of action and the selective differentiation of various analogs.

Conducting tests in human volunteers that show efficacy of the DIPA compounds for reducing skin dysesthesia caused by various dermatological disorders.

Conducting tests in human volunteers that show DIPA compounds, especially DIPA-1-7, is effective for relieving sensory discomfort of the skin, and thus may be used as an anti-nociceptive or anti-pruritic agent to treat dermatological disorders.

Applications

The DIPA compounds, when applied to keratinized skin, have sensory/cooling effects that mimic heat abstraction, but without a change in tissue temperatures. These compounds, can also penetrate the skin barrier, reach nerve endings in the epidermis and dermis, and enter the systemic circulation to exert cooling actions. These effects are obtained at small volumes, e.g., 0.1 to 0.5 mL, applied at a concentration of 1 to 20 mg/mL, or 0.1 to 2% wt/vol. The onset of effect is rapid, less than 5 minutes, and the sense of coolness is robust, refreshing, and strong. Compounds with similar bioactivity on the keratinized skin are not currently known or used in cosmetic or therapeutic applications. A number of new applications are possible with a molecule having such unusual properties.

For conditions of increased sensations of perceived heat stress, DIPA-1-7 can be used, for example, to increase athletic performance, to counteract the discomfort of vasomotor symptoms, and to counteract the discomfort of inflammation. In normothermic conditions, DIPA-1-7 applied to the facial skin may be used to enhance cognition and to alert and increase vigilance. DIPA-1-7 may also be used as a diagnostic agent for cold allodynia and hyperalgesia, as a laboratory reagent to characterize TRPM8 functions, and as an adjunct in the formulations of numerous topical pharmaceuticals. Furthermore, DIPA compounds can be used for dermatological disorders.

Heat Stress:

Thermal comfort is a technical term used by air-conditioning engineers to define "a state of mind in humans that expresses satisfaction with the surrounding environment." Maintaining thermal comfort for occupants of buildings or other enclosures is one of the important goals of architects and design engineers. For most people, the room temperature for thermal comfort is 25° C. (77° F.). Careful studies have documented that work performance and productivity (output/input) drop by 2% for every increment of +1° C. above 25° C. up to 33° C. At office temperatures of 28-30° C. (82-86° F.), there is increased sweating and complaints of headache, drowsiness and dullness, difficulty in concentrating, and physical discomfort. For example, studies have shown that increasing the indoor air temperature of a call center from 25° C. to 26° C. decreased the call response rate from 7.79 to 7.64 calls/hr, a 1.9% loss [Tanabe et al., 2007]. An ambient temperature above 25° C. is thus a form of heat stress.

Energy consumption of buildings in China account for at least one-quarter of the country's energy use, and sales of air-conditioning systems in Brazil and India are on an exponential increase. This rise in energy use has raised further concerns about global warming, but as most populations now work indoors, energy costs must be balanced against worker productivity. Basically, a worker's efficiency is better when he or she is kept cool. A method for combating mental lassitude from a hot environment, without incurring expenditures for energy, would have economic benefits. In the Case Studies describe herein, it was found that application of DIPA-1-7 to the facial skin of a student preparing for exams was useful in overcoming the discomforts of heat. The application of a DIPA-1-7 0.5% gel onto the facial skin, especially on the skin of the eyelids, and also on the skin of the neck, also provides relief from heat.

Athletic Performance

It is a natural desire of humans to want to perform better, either physically or mentally. Recently, there has been an enthusiastic surge of interest in the use of cryotherapy to improve athletic performance. Cryotherapy is defined as " . . . the lowering of tissue temperature (locally or generally) by the withdrawal of heat from the body to achieve a therapeutic objective . . . " External pre-cooling by heat abstraction, for example, by immersion in ice or by wearing a vest packed with ice, can improve work endurance in a hot environment (see, e.g., Marino et al., 2002). An increase in physical work output of ~5% can be shown for tasks of approximately 30 min [Grahn D A et al. Heat extraction through the palm of one hand improves aerobic exercise endurance in a hot environment. J Appl Physiol 99:972-978, 2005] Heat exhaustion limits work and this occurs when core body temperature approaches 40° C. (104° F.). Pre-cooling (or internal cooling, for example, by drinking an ice slurry) slows down the rate of heat accumulation.

Surprisingly, the improvement in athletic performance can be attained by increasing the perception of coolness, without modifying core temperature. Investigators showed that trained marathon runners wearing a commercial cooling collar (Black Ice LLC, Lakeland TN) extended the time to reach volitional exhaustion by 13.5% [Tyler et al. Cooling the neck region during exercise in heat. *J. Athletic Training*, 46, 61-68, 2011]. Cooling of the neck dampened the perceived level of thermal strain and delayed the point of voluntary termination of exercise. Participants tolerated a higher body temperature and heart rate when their neck regions were cooled.

In several studies with menthol, a chemical that produces sensations of coolness without a change in skin or core temperatures, it was noticed that an increased perception of cooling, without a change in core body temperature, may also enhance better physical performance. This effect was unexpected and attributed to menthol being a "positive" placebo [Gillis D J et al. The influence of menthol on thermoregulation and perception during exercise in warm, humid conditions. Eur J Appl Physiol 2010; 110:609-618; Schlader et al. The independent roles of temperature and thermal perception in the control of human thermoregulatory behavior. Physiol Behav 103:217-224, 2011]. The surface of the face is densely innervated with nerve endings that detect temperature. The peripheral cool/cold detection system is associated with specific nerve fiber discharges and precisely regulated so ±1° C. is easily discriminated. Over 92% of thermoceptive units on the face, especially around the lips, respond to cooling and these neurons are tonically active at room temperature (see, e.g., Hutchison et al., 1997).

It is likely than an agent such as DIPA-1-7 or DIPA-1-8, applied to the face, neck region, or chest will decrease heat discomfort and improve athletic performance.

Vasomotor Symptoms ("Hot Flushes/Night Sweats" in Post-Menopausal Women):

Flushing (vasodilation) and sweating occur on the body when the brain's thermoregulatory system perceives a need to lower body temperature. After menopause, at least one-third of women experience "hot flushes" (i.e., brief but repetitive episodes of feeling warm and flushed, and daytime and nighttime sweating). Replacement estrogens may alleviate symptoms but there are uncertainties if hormone replacement therapy (HRT) is safe. Sweating episodes that occur at night and in the early morning hours are especially inconvenient because the bed-sheets become wet and it is burdensome to change the bed-sheets on a daily or frequent basis. Episodes of "hot flushes/night sweats" can occur as often as on average 14 episodes per week. Aside from HRT, current alternative methods of therapy, such as yoga, acupuncture, and phytoestrogens, have limited if any effectiveness.

The DIPA compounds are potent agents that can cross the skin barrier and be absorbed into the bloodstream and exert systemic effects. One possible method of treating vasomotor symptoms may be to topically administer DIPA-1-6 or DIPA-1-7 via a controlled-release patch. The systemic effects of the DIPA compound will then give rise to cooling sensations to counteract activation of central heat-loss mechanisms (vasodilatation and sweating). The patch may be applied at night to a convenient location of the body, e.g., the skin above the supraclavicular fossa or the skin above the sternomastoid muscle, and the released DIPA compound would then inhibit the "night sweats." Alternatively, the DIPA compound (e.g., DIPA-1-5, DIPA-1-6, or DIPA-1-7) can be applied locally to the skin as a gel, lotion, or cream.

The best population for studying the possible benefits of DIPA therapy would be breast cancer survivor who cannot receive HRT. This patient population has severe problems with hot flushes.

Sensory Discomfort from Body Surfaces:

Topical application of DIPA compounds on skin refresh and invigorate the psyche. These analogs were further evaluated for anti-itch (and other anti-nociceptive) effects on skin. As shown in the Case Studies described herein, a 20 mg/mL solution, applied with a cotton-tipped applicator potently stopped itching and discomfort caused by contact dermatitis in three individuals. A most surprising recent event was the discovery that these compounds can act on intact skin to stop the discomforts of urticaria. Another surprise was the utility of these compounds for treating the itch of liver disease and cholestasis. The DIPA-1-7 was also effective against milaria rubra (prickly heat), and against a recalcitrant case of prurigo nodularis (a form of chronic atopic dermatitis). These results were surprising because there are no topical medications that work quickly against these conditions, especially urticaria and cholestatic itch.

A topical medication that can relieve skin discomfort has many applications in dermatological disorders including:
a) alleviation of irritation, itch and pain from various forms of dermatitis (atopic dermatitis, contact dermatitis, and irritant dermatitis, various forms eczema);
b) itch and discomfort from skin infections, insect bites, sunburn, photodynamic treatment of skin (e.g., actinic keratoses, basal cell carcinoma), lichen sclerosus;
c) pruritus due to xerosis [especially dry skin itch of the elderly], psoriasis, or seborrheic dermatitis;
d) pruritus ani, hemorrhoidal discomfort, pain from anal fissures, pain or itch from anal fistulas, pain from hemorrhoidectomy, perineal inflammation, anogenital skin inflammation and discomfort due to various local causes such as incontinence, diaper rashes, prickly heat rash, and perineal inflammation;
e) pain from burned, traumatized, diseased, anoxic, or irritated skin (e.g., skin damaged by laser surgery, diabetic ulcers, sunburn, radiation), and from procedures related to wound debridement and wound healing;
f) stomatitis, cheilitis, itching of the lips from cold sores or gingivitis;
g) vulval pruritus and pain (e.g., from candidiasis or idiopathic, such as vulva vestibulitis and vulvodynia), dyspareunia, anogenital infections, including warts and sexually transmitted diseases, fungal infections, viral infections of the skin (especially in immunocompromised patients);
h) nostril and nasal or upper airway discomfort from breathing obstruction, e.g., congestion, rhinitis, asthma, bronchitis, emphysema and chronic obstructive pulmonary diseases, dyspnea, sleep apnea and snoring; and
i) conjunctivitis, ocular surface irritation, pain from trauma and corneal abrasions, and pain from eye surgery.

Of special interest, is the use of DIPA-1-7 and DIPA-1-8 for scalp itch, e.g., in seborrheic dermatitis and psoriasis; these end-points being unmet medical needs. DIPA-1-7 may also be used to refresh the skin before application, or after removal of, cosmetics from the skin, to reduce the irritant effects of benzoyl peroxide in the treatment of acne, and to reduce sebum secretion and the appearance of an "oily" skin.

Breaking the Itch-Scratch Cycle

Itch (also called pruritus) is the sensation that causes the desire or reflex to scratch. Itch can be quite intense, and evokes obsessive behavior. For example, I have seen a person scratch his ankles until it bleeds because of the itch caused by insect bites (midges or sand flies). Scratching may have survival value because it rids fur-coated animals of parasites and insects on skin, but for humans excessive scratching exacerbates skin damage in dermatological disorders. That is, scratching injures the skin and the injury provokes more itch and scratching, a phenomenon called the "itch-scratch cycle".

MacDonald et al. has proposed a mechanism by which the itch-scratch cycle exacerbates tissue injury (Acta Dermato-Venereologica 97 (8): 1010, 2017). He stated that double-stranded RNA released from injured keratinocytes stimulates TOLL-3 receptors to generate more cytokines and chemokines, and thus inflammation is enhanced and perpetuated.

An anti-itch molecule may therefore not only provide symptomatic relief but also have a more subtle disease-modifying therapeutic effect in disorders such as atopic dermatitis wherein itch is localized and the itch-scratch cycle is a vicious contributor to the pathology of excoriations and lichenification. The irritated skin thickens and becomes chronically inflamed and fragile because of scratching, and is likely to breakdown with more scratching and rubbing. The ability to add a break to scratching is not restricted only to atopic dermatitis but also applicable to other dermatological disorders such as seborrheic dermatitis, acne or acneiform eruptions. Here, for example, the acne lesion is an inflammatory disorder of the sebaceous glands in the skin, and the subject picks and squeezes the lesions constantly. The mechanical damage to the inflamed skin aggravates the underlying tissue reactions. If a break can be applied to the tissue manipulation, then the lesion is given time to heal more quickly.

Itch prevents a good night's sleep and an atopic dermatitis patient will scratch themselves vigorously even when asleep. An effective medication should prevent itch within minutes after application and act sufficiently long to allow the subject to go to sleep. The subject should be instructed to apply the medication after washing, to use on an as-needed basis, and to apply thoroughly at night at sites of itch before sleep, because scratching can take place after the subject is asleep. This is especially important for children because the desire to scratch is instinctive and automatic, but will also damage the skin.

Pharmaceutical Adjunct

In pharmaceuticals or cosmeceuticals, the term "adjunct" is an additional substance, treatment, or procedure used for increasing the efficacy or safety of the primary substance, treatment, or procedure or for facilitating its performance. The DIPA compounds relieve sensory discomfort of the skin, have anti-nociceptive activity, and are active at less than 1 minute after application. They are ideal adjuncts for pharmaceuticals and for cosmetics applied to the skin.

If the primary substance is an irritant, the adjunct may be used to decrease irritancy, and hence improve patient tolerance and compliance. For example, an adjunct such as DIPA-1-7 can be added an anti-acne preparation containing benzoyl peroxide. Benzoyl peroxide, the primary substance, works as a skin peeling agent, increases cell turnover, and reduces P. acnes, but it is an irritant and can cause burning, swelling, and pain when applied to the skin. Similarly, imiquimod (Aldara®), which is used as a primary substance to treat genital warts and skin cancer can cause blistering and pain, and an adjunct such as DIPA-1-7, DIPA-1-8 or DIPA-1-9 may increase patient acceptance and compliance in the use of this drug.

An adjunct such as DIPA-1-7 may be used to increase the "apparent" efficacy of another primary ingredient, and thereby improve patient satisfaction and adherence to a dosage schedule. For example, DIPA-1-7 at about 0.5 to 2%, stops itching within minutes after application. If combined with an anti-inflammatory steroid, the preparation may be more desirable than the anti-inflammatory steroid alone, which takes longer to act. Anti-inflammatory steroids, such as hydrocortisone, triamcinolone, and clobetasol are used for sensory discomfort of the skin in disorders such as insect stings, contact dermatitis, atopic eczema, and psoriasis. The presence of DIPA-1-7 as an adjunct, in addition to helping to stop the itch, may help reduce the dose or the frequency of application of the primary ingredient, yet achieve an equivalent therapeutic effect. This adjunct benefit will be especially beneficial in the use of skin steroids because of the well-known undesirable effects of collagen degradation, tissue thinning, and increased susceptibility to infections. An adjunct that reduces dosage or promote greater efficacy of the primary ingredient has value. Other primary anti-pruritics are aluminum acetate, and strontium chloride or strontium nitrate.

For skin disorders, compositions of the present discovery may also be used as adjuncts for procedures such as phototherapy, laser therapy, cryotherapy, or UV-therapy of the skin.

Pharmaceuticals that may be used, in combination or in sequence with adjunct DIPA compounds include anti-inflammatory steroidal agents, anti-inflammatory analgesic agents, antihistamines, sympathomimetic amine vasoconstrictors, local anesthetics, antibiotics, anti-acne agents, topical retinoids, drug for genital warts and skin cancer, drugs for wrinkles and ageing skin, anti-hemorrhoidal agents, drugs for vulvar itch, drugs to stimulate hypertrichosis, skin moisturizers, and agents for keratolysis.

Examples of steroidal anti-inflammatory agents include hydrocortisone, clobetasol, clobetasol propionate, halobetasol, prednisolone, dexamethasone, triamcinolone acetonide, fluocinolone acetonide, fluocinonide, hydrocortisone acetate, prednisolone acetate, methylprednisolone, dexamethasone acetate, betamethasone, betamethasone valerate, flumetasone, fluticasone, fluorometholone, beclomethasone dipropionate, etc.

Examples of anti-inflammatory analgesic agents include methyl salicylate, monoglycol salicylate, aspirin, indomethacin, diclofenac, ibuprofen, ketoprofen, naproxen, pranoprofen, fenoprofen, sulindac, fenclofenac, clidanac, flurbiprofen, fentiazac, bufexamac, piroxicam, pentazocine, etc.

Examples of antihistamines include azelastine hydrochloride, diphenhydramine hydrochloride, diphenhydramine salicylate, diphenhydramine, chlorpheniramine maleate, promethazine hydrochloride, etc.

Examples of sympathomimetic amine vasoconstrictors include phenylephrine hydrochloride, oxymetazoline, naphazoline, and other imidazoline receptor agonists used for nasal decongestant activity and for redness and vasodilatation on the ocular surfaces.

Examples of skin moisturizer ingredients include the three categories of humectants, emollients and preservatives. Humectants, such as urea, glycerin and alpha hydroxy acids, help absorb moisture from the air and hold it in the skin. Emollients, such as lanolin, mineral oil and petrolatum, help fill in spaces between skin cells, lubricating and smoothing the skin. Preservatives help prevent bacteria growth in moisturizers. Other ingredients that moisturizers may contain include vitamins, minerals, plant extracts and fragrances.

Example of an agent for hypertrichosis is bimatoprost.

Study 1

Toxicity

Preliminary toxicological studies were conducted on DIPA 1-7. It was not mutagenic in the Ames test (Strains TA 98 and TA100, with and without liver activation) (tests conducted by Apredica, Watertown, MA, USA).

DIPA-1-7, dissolved in 3% ethanol/97% 1,2-propanediol, or vehicle alone, was administered at 20 mg/kg perioral for 7 days (n=10 per group) to male rats, and on the $8^{th}$ day, the animals were euthanized with sodium pentobarbital and the major organs (body, heart, liver, lungs, kidney, testes, brain) were removed and weighed. Heart tissues (ventricle and heart valves) and liver samples were stained with hematoxylin and eosin and the histology examined. There was no significant difference in body or organ weights between the two groups and the heart and liver histology were normal.

Study 2

Tissue Temperature

The compounds of the present discovery simulate the sensations of heat abstraction, but do not alter tissue temperatures. The average forehead skin temperature of subjects (N=5) was measured following application of DIPA-1-7 (with a wipe at a concentration of 20 mg/mL in distilled water) to the forehead skin. The results are summarized in Table 5. The subjects noted the cooling effect of DIPA-1-7 on the skin which lasted for 30-45 minutes; however, skin temperatures were not affected.

TABLE 5

Skin temperatures of human forehead after DIPA-1-7, 20 mg/mL.

| Time | Temperature (° C.) | |
|---|---|---|
| | Control | DIPA-1-7 |
| Before | 37.3 | 37.4 |
| 0 minutes | 37.2 | 37.4 |
| 15 minutes | 37.5 | 37.5 |
| 30 minutes | 37.1 | 37.1 |
| 45 minutes | 37.4 | 37.2 |
| 60 minutes | 37.0 | 37.1 |

Study 3

Sensory Effects of Compounds on Facial Skin

When a test compound is applied to the skin, it is possible to characterize the resulting sensations. The quality of the sensations produced by individual compounds favours certain characteristics that are distinct. The quality of the sensations evoked, their descriptors, and their proposed mechanism of action, are summarised in Table 6. For any compound, there may be some overlap in activity, but usually one compound occupies only one or two categories of sensations. For example, icilin is exclusively cool, with very little "cold". DIPA-1-6 and DIPA-1-7 are exceptional in producing pleasant, robust "dynamic cool." DIPA-1-8 and DIPA-1-9 are strong cold-producing agents.

TABLE 6

Descriptor and proposed mechanisms of DIPA compounds on skin.

| Type of Sensation | Descriptor | Proposed Mechanisms on Sensory Neurons |
|---|---|---|
| Inactive | No effect | — |
| Cool, steady and pleasant | Cool | Balanced stimulation of static and dynamic |
| Cold, constant, but limited by desensitization | Cold | Higher stimulation of static |
| Dynamic cooling, robust cool/cold, strong refreshing | Dynamic cool | Higher stimulation of dynamic |

TABLE 6-continued

Descriptor and proposed mechanisms of DIPA compounds on skin.

| Type of Sensation | Descriptor | Proposed Mechanisms on Sensory Neurons |
|---|---|---|
| Stinging cold, sometimes with irritation | Icy cold | Stimulation of dynamic and static, and also nociceptive sites |

Even after the offset of the cooling/cold action, some of the compounds have a "reservoir effect." Experimentally, this is measured 1 hour after offset by placing a hot and then a cold towel over the site of application and determining if the onset of cooling/cold returns for at least 30 minutes. If this occurs, then there is a positive "reservoir effect". The "reservoir effect" can also be provoked with air movement, but the conditions for air movement are difficult to standardize. The "reservoir effect" of DIPA-compounds in skin is most likely due to residual drug that is reactivated to stimulate dynamic/static sensory neurons.

In the studies described herein, the sensation of coolness/cold is rated as 0, 1, 2, or 3 with: 0 as no change; 1 as slight coolness, or cold; 2 as clear-cut signal of coolness or cold; and 3 as strong cooling or cold. The sensations are recorded at intervals of 5 to 15 minutes, until at least two successive zeroes are obtained.

The onset of drug action is taken as the time to reach 2 units of coolness intensity.

The duration of sensory action is defined as the offset time minus the onset time. The offset of drug action is defined here as the time when coolness intensity drops below 2, after previously surpassing 2 units. An inactive compound is defined as one that does not exceed 2 units of cooling for 5 minutes or more after application. The offset endpoint is sometimes unstable for compounds that act for two or more hours, because the coolness/cold sensation may fluctuate due to environmental variables such as sunlight, ventilation, activity, and the "reservoir effect." For example, DIPA-1-8 and 2-8 are exceptionally long-acting on the skin.

The effects of test compounds on facial skin were determined. Compounds were tested on zygomatic. Test compounds were applied to the skin of the zygomatic using cotton gauze (0.4 g, rectangular, 50 mm×60 mm; from CS-being, Daisan Cotton, Japan). The test compounds were used at a concentration of 20 mg/mL in distilled water. The onset and duration of the sensory effect was measured with a stopwatch. The degree of "dynamic cool" was graded from 0 to +++, with intermediate steps of + and ++. An anti-fatigue effect was present only if there was sufficient "dynamic cool." The results are summarized in Table 7 & 8.

TABLE 7 & 8

Sensory effects after application to zygomatic and forehead skin.

| Code | $R_3$ | Carbon atoms | Onset (min) | Sensory Quality | Anti-Fatigue | Duration (hr) | Reservoir Effect |
|---|---|---|---|---|---|---|---|
| DIPA-1-5 | 5 | 11 | ~1 | dynamic | 0 | 0.5 | No |
| DIPA-1-6 | 6 | 12 | ~1 | dynamic | ++ | 1.3 | Yes |
| DIPA-1-7 | 7 | 13 | ~1 | dynamic-icy | +++ | 3.2 | Yes |
| DIPA-1-8 | 8 | 14 | ~1 | cold-icy | ++ | 4.0 | Yes |
| DIPA-1-9 | 9 | 15 | ~2 | cool | 0 | 2.0 | No |
| 2-4 | 4 | 12 | ~1 | cool | 0 | 0.3 | No |
| 2-5 | 5 | 13 | ~1 | cool | 0 | 1.1 | Yes |
| 2-6 | 6 | 14 | ~2 | cold | + | 1.5 | Yes |

TABLE 7 & 8-continued

Sensory effects after application to zygomatic and forehead skin.

| Code | R₃ | Carbon atoms | Onset (min) | Sensory Quality | Anti-Fatigue | Duration (hr) | Reservoir Effect |
|------|-----|------|------|------|------|------|------|
| 2-7 | 7 | 15 | ~2 | cold | + | 2.4 | Yes |
| 2-8 | 8 | 16 | 5 | cold | 0 | 5.6 | Yes |

Each of 3-1 and 3-2 was also tested and found to be inactive on periorbital, and zygomatic/forehead skin.

For further comparisons, the newly synthesized "mixed" 1-isopropyl-sec-butyl-phosphorylalkanes (3,4-6, 3,4-7, 3,4-8 and 3,4-9) were tested on zygomatic skin (FIG. 1). The test procedures were modified because of the limited quantities of these analogs. To deliver the solution to the skin, a 80%-polyester-20%-viscose rayon wipe was cut into squares (7×8 cm, 0.45 g each) and a precise volume (2.5 mL) of test solution is added to the wipe using a dropper bottle. Delivery and scoring of effect. An average 74±2 μL volume containing the test ingredient was wiped onto the receptive fields of the nerves on the zygomatic process (cheek-bone). As before, the sensory effects of cool/cold were recorded at 5 and 10 min intervals. Quarter and half point scores are allowed. Scoring is stopped when two zeroes are observed in a 10 min interval. At least four trials are conducted for each concentration with two to three volunteer test subjects for each compound.

Figure 2:
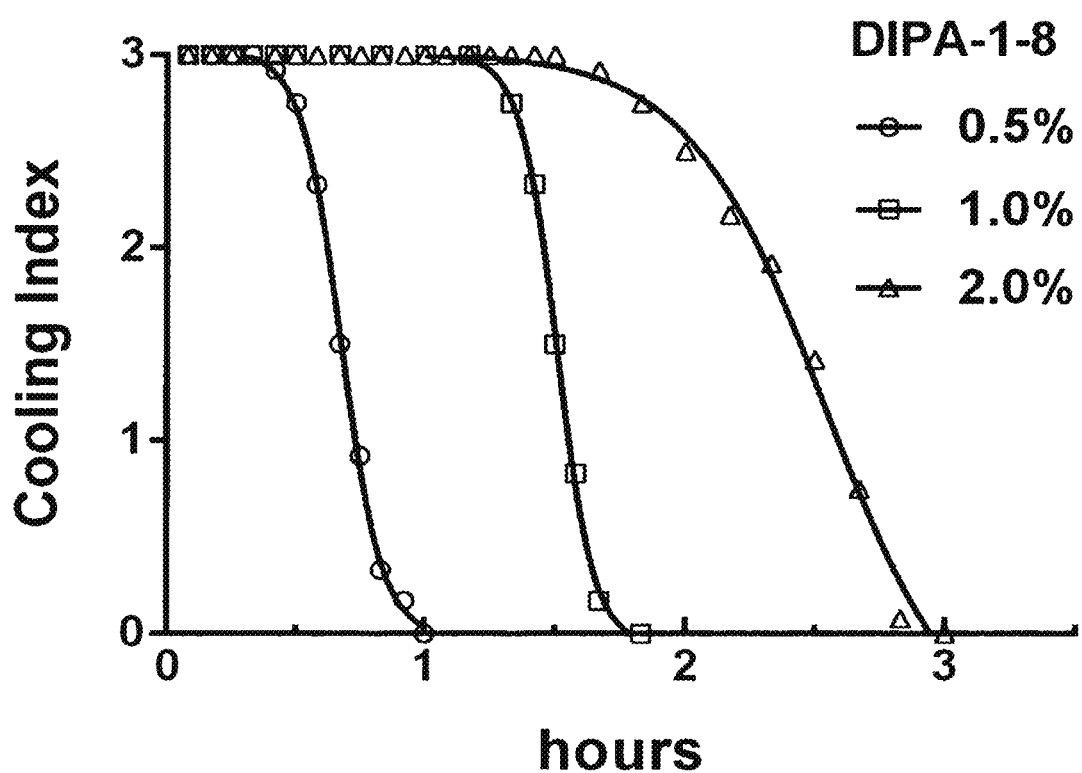
FIG. 2. shows the cooling sensations evoked by topical wiping of different concentrations of DIPA-1-8 onto the skin above the zygomatic process. The cooling activity can be measured as the intensity/duration area-under-curve (AUC) or as time for half maximal effect ($T_{-1/2}$), using software of the GraphPad Prism package. The graph shows the dose-response curve for the compound DIPA-1-8 applied at 0.5, 1 and 2% (5, 10, and 20 mg/mL dissolved in distilled water).

Results from the testing of DIPA-1-8 at three concentrations is shown in FIG. 2.

FIG. 2. shows the cooling sensations evoked by topical wiping of different concentrations of DIPA-1-8 onto the skin above the zygomatic process. The cooling activity can be measured as the intensity/duration area-under-curve (AUC) or as time for half maximal effect ($T_{-1/2}$), using software of the GraphPad Prism package. The graph shows the AUC dose-response curve for the compound DIPA-1-8 applied at 0.5, 1 and 2% (5, 10, and 20 mg/mL dissolved in distilled water).

Figure 3:
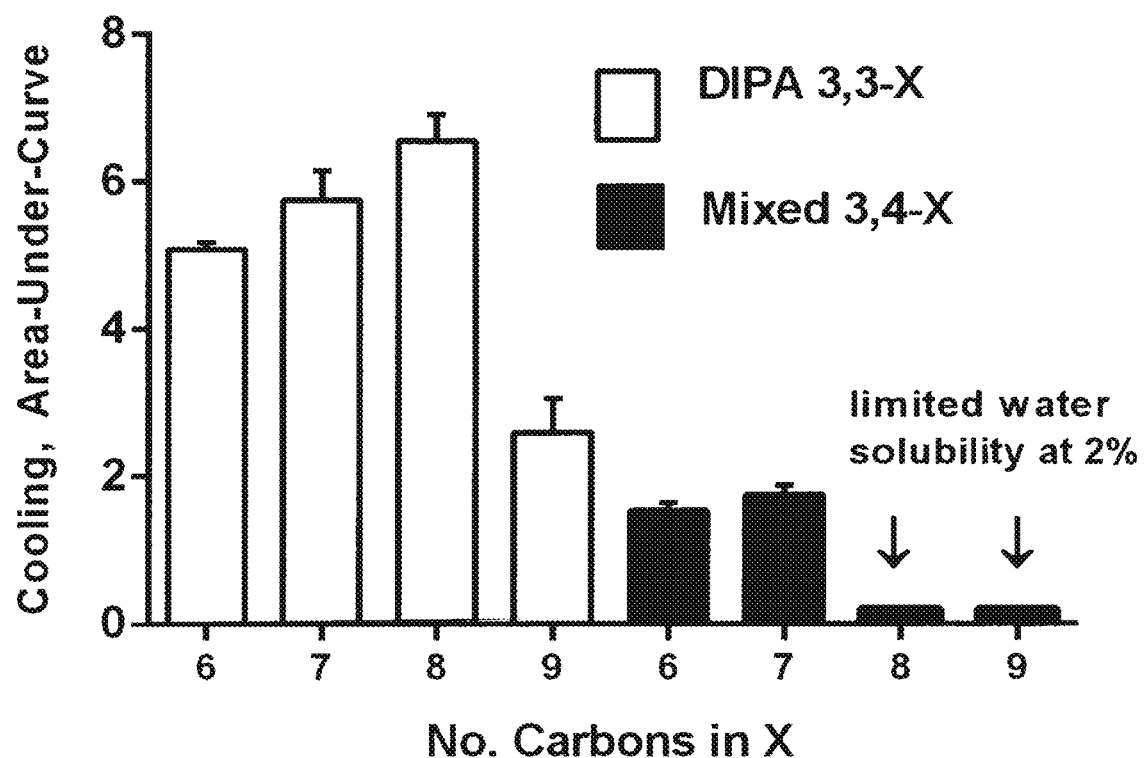
FIG. 3. shows the cooling sensations evoked by topical wiping of different compounds onto the skin above the zygomatic process. The cooling activity is expressed as the integrated intensity/duration area-under-curve (AUC), using software of the GraphPad Prism package. Test concentration was 2% (20 mg/mL in distilled water). The diisopropyl analogs are DIPA 3,3-X and isopropyl, sec-butyl analogs are Mixed 3,4-X. The "X" refers to the number of carbons on the third alkyl group. It can be seen that the Mixed analogs are much less active on the cheekbone skin than the corresponding diisopropyl analogs.

A comparison of the DIPA diisopropyl analogs (3,3-X) versus the mixed propyl-sec-butyl analogs (3,4-X) are shown in FIG. 3. Statistical significant difference (P<0.01) are seen between 3,3-x and the asymmetrical chiral 3,4-x analogs. The 3,4-8 and 3,4-9 formed a milky/small oil droplet emulsion at 20 mg/mL.

Notably, DIPA-1-7 selectively produced the unusual sensation of "dynamic cool" and also had anti-fatigue effects. From the data shown above, it can be seen that, among these compounds, DIPA-1-7 evoked "dynamic cool" on both periorbital and zygomatic/forehead surface. Another compound with similar properties was DIPA-1-8, but this compound is was more cold/icy cold, although it had the desirable property of a longer duration of action on the zygomatic/forehead surface. The long duration of action of DIPA-1-7 and DIPA-1-8 on the skin adds value as an anti-fatigue agent, especially for the fatigue of chronic illness. As shown in the case studies described below, a single application of DIPA-1-7 is sufficient to counteract fatigue and heat stress for at least three to four hours.

A special value of DIPA-1-9 is the comfortable cooling it provides and its long duration of action after zygomatic and periorbital application, and the absence of any stinging. Thus, it has a special therapeutic niche for the relief of skin discomfort.

The results here for the selective attributes of DIPA-1-7 and DIPA-1-8 are unexpected, surprising, and has practical applications for counter-acting fatigue and anti-nociception. A special value of DIPA-1-9 is the comfortable cooling it provides and its long duration of action after periorbital application, and the absence of any stinging. Thus, it has a special therapeutic niche for the relief of ocular discomfort.

Study 4

Agonist Activity of Compounds on TRPM8

The in vitro effects of a first set of test compounds (Table x) were evaluated on cloned hTRPM8 channel (encoded by the human TRPM8 gene, expressed in CHO cells) using a Fluo-8 calcium kit and a Fluorescence Imaging Plate Reader (FLIPR$^{TETRA}$™) instrument. The assays were conducted by ChanTest Corporation (14656 Neo Parkway, Cleveland, OH 44128, USA).

Test compounds and positive control solutions were prepared by diluting stock solutions in a HEPES-buffered physiological saline (HBPS) solution. The test compound and control formulations were loaded in polypropylene or glass-lined 384-well plates, and placed into the FLIPR instrument (Molecular Devices Corporation, Union City, CA, USA). The test compounds were evaluated at 4 or 8 concentrations with n=4 replicates per determination. The positive control reference compound was L-menthol, a known TRPM8 agonist. The test cells were Chinese Hamster Ovary (CHO) cells stably transfected with human TRPM8 cDNAs.

For FLIPR$^{TETRA}$™ assay, cells were plated in 384-well black wall, flat clear-bottom microtiter plates (Type: BD Biocoat Poly-D-Lysine Multiwell Cell Culture Plate) at approximately 30,000 cells per well. Cells were incubated at 37° C. overnight to reach a near confluent monolayer appropriate for use in a fluorescence assay. The test procedure was to remove the growth media and to add 40 μL of HBPS containing Fluo-8 for 30 minutes at 37° C. 10 μL of test compound, vehicle, or control solutions in HBPS were added to each well and read for 4 minutes.

Concentration-response data were analyzed via the FLIPR Control software that is supplied with the FLIPR System (MDS-AT) and fitted to a Hill equation of the following form:

$$\text{RESPONSE} = \text{Base} + \frac{\text{Max} - \text{Base}}{1 + \left(\frac{xhalf}{x}\right)^{rate}}$$

where: "Base" is the response at low concentrations of test compound; "Max" is the maximum response at high concentrations; "xhalf" is the $EC_{50}$, the concentration of test compound producing half-maximal activation; and "rate" is the Hill coefficient. Nonlinear least squares fits were made assuming a simple one-to-one binding model. The 95% Confidence Interval was obtained using the GraphPad Prism 6 software. The results are summarized in Table 9.

TABLE 9

$EC_{50}$ and relative potency of compounds on TRPM8..

| Code | $EC_{50}$ μM | 95% Confidence Interval | Relative Potency |
|------|------|------|------|
| Menthol | 3.8 | 2.5 to 5.6 | 1.0 |
| DIPA-1-5 | 5.6 | 4.4 to 7.2 | 0.7 |
| DIPA-1-6 | 2.4 | 1.5 to 4.0 | 1.6 |

TABLE 9-continued

EC$_{50}$ and relative potency of compounds on TRPM8..

| Code | EC$_{50}$ μM | 95% Confidence Interval | Relative Potency |
|---|---|---|---|
| DIPA-1-7 | 0.7 | 0.5 to 1.0 | 5.4 |
| DIPA-1-8 | 0.7 | 0.5 to 1.0 | 5.4 |
| DIPA-1-9 | 0.9 | 0.4 to 2.5 | 4.0 |
| 2-4 | 14.5 | 7 to 29 | 0.3 |
| 2-5 | 1.7 | 1.0 to 2.9 | 2.2 |
| 2-6 | 0.8 | 0.5 to 1.3 | 4.7 |
| 2-7 | 1.1 | 0.6 to 2.3 | 3.4 |
| 2-8 | 1.3 | 0.7 to 2.3 | 2.9 |
| 3-1 | 24 | 8 to 76 | 0.2 |
| 3-2 | 4.2 | 1.6 to 10.8 | 0.9 |

Of the 12 compounds tested, all showed full efficacy on the TRPM8 receptor, i.e., at higher tested concentrations there was ~100% stimulation of calcium entry, and the data fitted a sigmoidal dose-response curve. The results for the "di-isopropyl" compounds of this invention are illustrated in FIG. 3.

FIG. 3 is a graph of response (Relative Fluorescence Units; % of maximum) as a function of the logarithm of the concentration of the test compound (denoted agonist), expressed in μM, for each of DIPA-1-5 (circles), DIPA-1-6 (squares), DIPA-1-7 (inverted triangle), DIPA-1-8 (diamonds), or DIPA-1-9 (up-right triangle).

The EC$_{50}$ of the more potent compounds (DIPA-1-7, DIPA-1-8, DIPA-1-9, 2-5, 2-6, 2-7, 2-8) fell within a narrow range with overlapping 95% Confidence Intervals. The potency of DIPA-1-7, DIPA-1-8, and DIPA-1-9 are similar and significantly greater than the potencies of DIPA-1-5 and DIPA-1-6. By contrast the structural modifications of comparative compounds 3-1 and 3-2 resulted in a significant loss of bioactivity To examine the specificity of the test compounds, further studies were conducted on TRPV1 channels (human TRPV1 gene expressed in HEK293 cells) and TRPA1 channels (human TRPA1 gene expressed in CHO cells). The test cells were Chinese Hamster Ovary (CHO) cells or Human Embyronic Kidney (HEK) 293 cells transfected with human TRPV1 or TRPA1 cDNAs. The positive control reference compound was capsaicin (a known TRPV1 agonist) or mustard oil (a known TRPA1 agonist). DIPA-1-7 and DIPA-1-8 did not exhibit any agonist on antagonist activity on TRPA1 channels at maximum tested concentrations of 100 μM. A weak TRPV1 agonist activity was found for DIPA-1-7, but this was not dose-dependent.

In bioactivity studies, potency was not correlated to the TRPM8 EC$_{50}$. For example, DIPA-1-5 and DIPA-1-6 are more potent in producing shaking behavior than DIPA-1-7 and DIPA-1-8 [see Study 6]. There were no distinguishing features in the TRPM8 EC$_{50}$ data which enabled prediction of which compounds have potent "dynamic cool" properties in vivo.

Further tests were conducted on "mixed" isopropyl-sec-butylphosphorylhexane and heptane analogs. The data were collected by Andersson et al. of King's College, London, UK, using his methods described in "Modulation of the cold-activated channel TRPM8 by lysophospholipids and polyunsaturated fatty acids. Journal Neuroscience 27 (12): 3347-3355, 2007. Here, the cellular entry of the calcium-sensitive dye Fura-2 was used to study the effect of the test compounds on TRPM8 expressed in Chinese hamster ovary cells. Cells, grown in culture, were seeded at an approximate density of 30,000 cells/well overnight, and loaded for ~1 hr with 2 M Fura-2 (Molecular Probes, Leiden, The Netherlands), and then placed on glass coverslips. Test solutions were added with a micropipette positioned close to the cells. Emission intensity from cells was measured for 90 sec, at every 4 or 5 sec, using excitation wavelengths of 340 and 380 nm and an emission of 520 nm. Fluorescence emission intensity ratios at 340 nm/380 nm excitation (R, in individual cells) were recorded with a FlexStation and the ImageMaster suite of software (PTI, South Brunswick, N.J.). Samples were tested in triplicate at each concentration and the averaged values analyzed by non-linear regression using an a sigmoidal function fit of the points to obtain an estimated EC50 (median effective concentration) (GraphPad Prism software, La Jolla, California).

Figure 4:
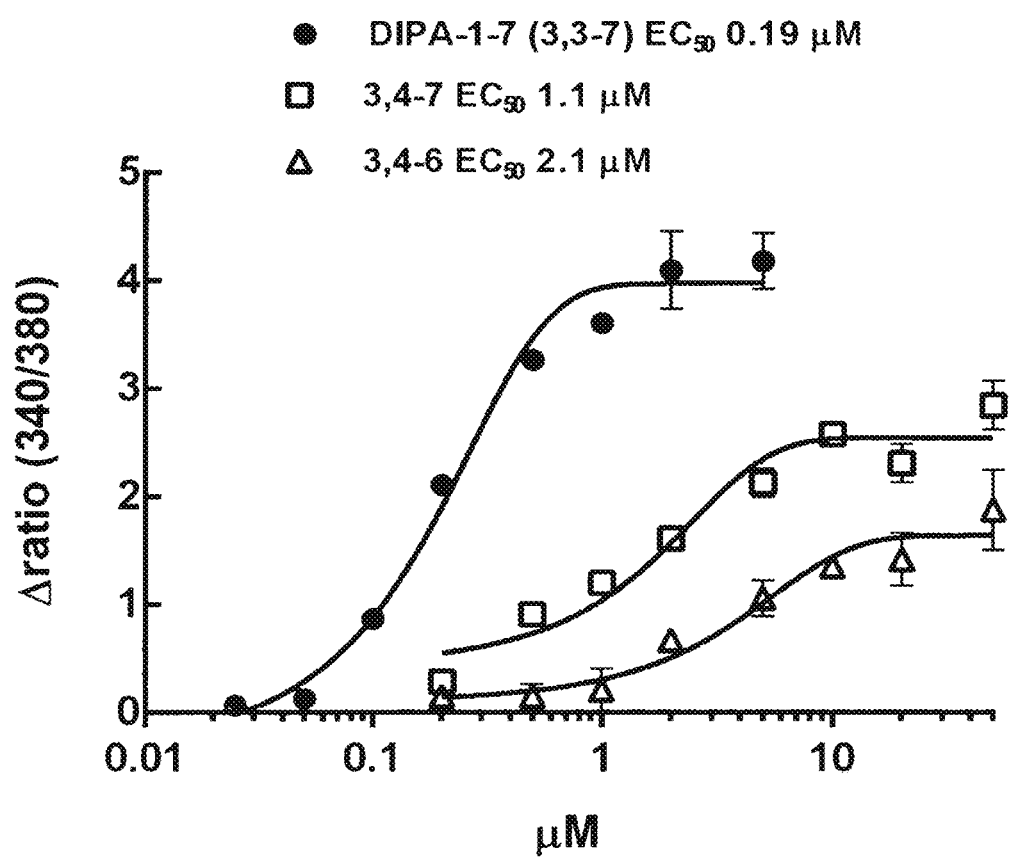
FIG. 4. Is a graph of fluorescence response (Δ ratio 340/380) in TRPM8 transfected cells as a function of the logarithm of the concentration of the test compound, expressed in μM, for DIPA-1-7 (black circle), 3,4-7 (open squares), or 3,4-6 (open triangles). The assays were conducted by Andersson et al. of King's College, London, UK, using his methods described in "Modulation of the cold-activated channel TRPM8 by lysophospholipids and poly-unsaturated fatty acids. Journal Neuroscience 27 (12): 3347-3355, 2007.

The potency of three analogs for activation of TRPM8 (cooling receptor) in transfected cells is shown in FIG. 4. The units (Δ ratio) on the ordinate measures entry of fluorescent calcium probes into transfected cells.

FIG. 4. is a graph of fluorescence response (Δ ratio 340/380) in TRPM8 transfected cells as a function of the logarithm of the concentration of the test compound, expressed in μM, for DIPA-1-7 (black circle), 3,4-7 (open squares), or 3,4-6 (open triangles). The assays were conducted by Andersson et al. of King's College, London, UK, using his methods described in "Modulation of the cold-activated channel TRPM8 by lysophospholipids and poly-unsaturated fatty acids. Journal Neuroscience 27 (12): 3347-3355, 2007.

The 3,3-7 (DIPA-1-7) is substantially more potent (~10× and ~5×) than 3,4-6 and 3,4-7. Note that 3,4-6 and 3,4-7 species do not reach the same degree maximal efficacy on activation of the receptor, even at supra-maximal concentrations.

From these results, it appears that the EC$_{50}$ values do not give information on the quality of the heat abstraction sensation, the duration of action, or the accessibility of the molecule to tissue targets. The identification of selective agents requires bioassays that more directly address these questions.

Study 5

Studies on Isolated Vagus Nerve: Direct Anti-Nociceptive Activity

To determine if DIPA-1-7 acted directly on sensory nerves, it was tested in an isolated nerve model developed at the Imperial College, London, U.K. [Birrell et al. TrpA1 agonists evoke coughing in guinea pig and human volunteers. Amer. J. respiratory and critical care medicine 180, 1042-7, 2009; Patel, H. J. et al. Inhibition of guinea-pig and human sensory nerve activity and the cough reflex in guinea-pigs by cannabinoid (CB2) receptor activation. Brit. J. Pharmacol. 140, 261-8, 2003]. In this in vitro assay, segments of the mouse vagus nerve are placed on a platform and the electrical activity is recorded after topical application of capsaicin. Capsaicin is a known irritant that elicits pain when it is applied to the skin and it will depolarize the isolated vagus. The ability of substances to inhibit this capsaicin-induced depolarization is measured.

Briefly, segments of vagus nerve, caudal to the nodose ganglion, were removed from mice with fine forceps and segments placed in oxygenated Krebs solution and bubbled with 95% $O_2$/5% $CO_2$. The desheathed nerve trunk was mounted in a 'grease-gap' recording chamber and constantly superfused with Krebs solution with a flow rate of approximately 2 mL/min, and the electrical activity of the nerve monitored with electrodes. The temperature of the perfusate was kept constant at 37° C. by a water bath. Nerve depolarizations were induced by superfusion of the nerve with capsaicin (1 µM). After two reproducible depolarization responses to capsaicin, DIPA-1-7 was applied at 1 mg/mL (4 µM) for 10 minutes in the perfusate followed by capsaicin. The nerves were then washed with Krebs until the responses had returned to baseline and challenged again with capsaicin. The results and tracings obtained in normal and TRPM8 knockout mouse are shown in FIG. 5.

FIG. 5 shows chart traces that illustrate, in the first trace ("Wild Type"), the inhibition of capsaicin-induced depolarization of the isolated mouse vagus by DIPA-1-7, superfused at a concentration of 1 mg/mL, and, in the second trace ("TRPM8 KO"), the significant absence of inhibition in the isolated TRPM8 KO (knockout) mouse vagus by DIPA-1-7, superfused at a concentration of 1 mg/mL.

In the tracings shown in the FIG. 5, the first two peaks show the depolarization response of the mouse vagus to capsaicin ("Caps"). After DIPA-1-7 is applied (1 mg/mL), the response is suppressed in the normal mouse vagus ("Wild Type"), but not in the TRPM8 knock-out ("TRPM8 KO") mouse vagus.

The percent inhibition of capsaicin-induced depolarization of the isolated normal mouse vagus caused by DIPA-1-7 was about 75%; the percent inhibition of capsaicin-induced depolarization of the isolated TRPM8 knock-out mouse vagus caused by DIPA-1-7 was about 20%.

This experiment clearly demonstrates a direct peripheral pharmacological action of the DIPA-1-7 on the sensory nerve, which is a surprising and unexpected result. Normally, one thinks of cold transduction gating the nociceptive signals in the central nervous system. That is, coolness felt in the brain inhibits the perception of pain and discomfort in the brain. Here, we find a direct peripheral mechanism of action, suggesting that transduction of the pain signal is impaired by DIPA-1-7 in the peripheral nerve. Furthermore, the diminished response in the TRPM8 KO mouse indicated that the receptor target was TRPM8. These results provide strong evidence that DIPA-1-7 can be used as a peripheral anti-nociceptive agent and the target receptor is TRPM8.

Capsaicin is a TRPV1 agonist and the search for an effective TRPV1 antagonist has been the super-intense quest of many pharmaceutical companies for the past ten or more year. Here, it is shown that DIPA-1-7 is an effective "physiological" antagonist of TRPV1 at low concentrations. DIPA-1-7, by itself, did not evoke depolarization, indicating that it is free of agonist activity at this "pain" receptor. These results strongly indicate the usefulness of DIPA-1-7 as an anti-nociceptive agent.

Study 6

Activity in Laboratory Rat: Perioral and Topical Delivery

Fur-coated and feathered animals—when wet and cold—shake, like a wet dog (see, e.g., Dickerson et al., 2012; Ortega-Jimenez et al., 2012; Wei, 1981). These shakes are rapid alternating contractions of the supination and pronation muscles about the spinal axis, and can be readily observed and counted. "Wet-dog shaking" has been studied in detail in animals and this behaviour is interpreted to have survival value because shaking, by removing the water off the skin, reduces the need to expend evaporative energy to remove wetness. The triggering sensation for shaking is thus having water trapped in between hair follicles or feathers. Humans have little hair on skin and normally do not shake, but this wet shaking can be mimicked by some individuals who exit a cold swimming pool. The likely equivalent behaviour to shaking in humans is shivering, a condition caused by generalized sensations of coolness/cold and wetness.

Drug-induced shaking in animals has been reviewed (see, e.g., Wei, 1981). Under the right conditions, drug-induced shaking can be observed in the pentobarbital-anesthetized rat, enhanced by hypothermia and cold, and inhibited by elevating body temperature.

Test compounds were evaluated for "wet-dog shaking" as a model of dynamic cooling. Using a standardized procedure, test compounds were compared in their ability to stimulate the shaking response by perioral administration and by topical delivery to the abdominal skin Perioral. Test compounds were dissolved in saline and administered by oral gavage to pentobarbital-anesthetized male albino rats at 20 mg/kg at a volume of 0.1 mL/100 g body weight [N=3 to 4 rats per compound]. Shaking was counted over a 40 min period and recorded at 10-min intervals.

Three of the four "di-isopropyl" compounds caused vigorous shaking. The "di-sec-butyl" compounds were relatively inactive, except 2-5 which elicited an average of 4 shakes in the 40 min observation period. By contrast, DIPA-1-5, DIPA-1-6, and DIPA-1-7 produced an average shaking frequency of 86, 56, and 36 shakes, respectively. The strong activity of DIPA-1-5 was unusual. Applied to the skin, DIPA-1-5 has a refreshing "dynamic cool", but the duration of action of only about 30 min was significantly less than that for DIPA-1-6 and DIPA-1-7. The shorter duration of action of DIPA-1-5 limits its practical utility. It is possible that its smaller molecular size facilitates absorption and allows greater access to systemic receptors, and therefore more shaking.

The relationship of the shake response to temperature sensation was further studied [in pentobarbital-anesthetized rats]. After injection of the anesthetic, rectal temperature drops, and reaches approximately 35° C. in about 10 min. This hypothermia can be reversed by placing the animal on a heated surface and body temperature maintained at 38° C. DIPA-1-7 20 mg/kg perioral elicited 36±5 shakes (N=6) in the anesthetized rat, but in the heated animals, the shaking frequency was significantly reduced to 5±2 shakes (N=6) [$P<0.001$]. The reduction of shaking frequency by ⅔ under heat indicated that the shake response was linked to cold sensations and shivering.

Topical. Shaking is an excellent indicator of in vivo effect. Methods were developed to determine if shaking was seen after topical application of DIPA compounds. The abdominal skin of the pentobarbital-anesthetized rat was shaved and 20 µL of the pure unadulterated DIPA chemical was applied with a micropipette on a ~1 cm diameter circle of skin, enclosed with a ring of cream [Baby cream "Nevskaya kosmetika Detskyi" Nevskaya Kosmetika Inc., Saint-Petersburg 192029], as shown in the FIG. 6. The number of shakes was counted for 1 hr after application.

Figure 6:
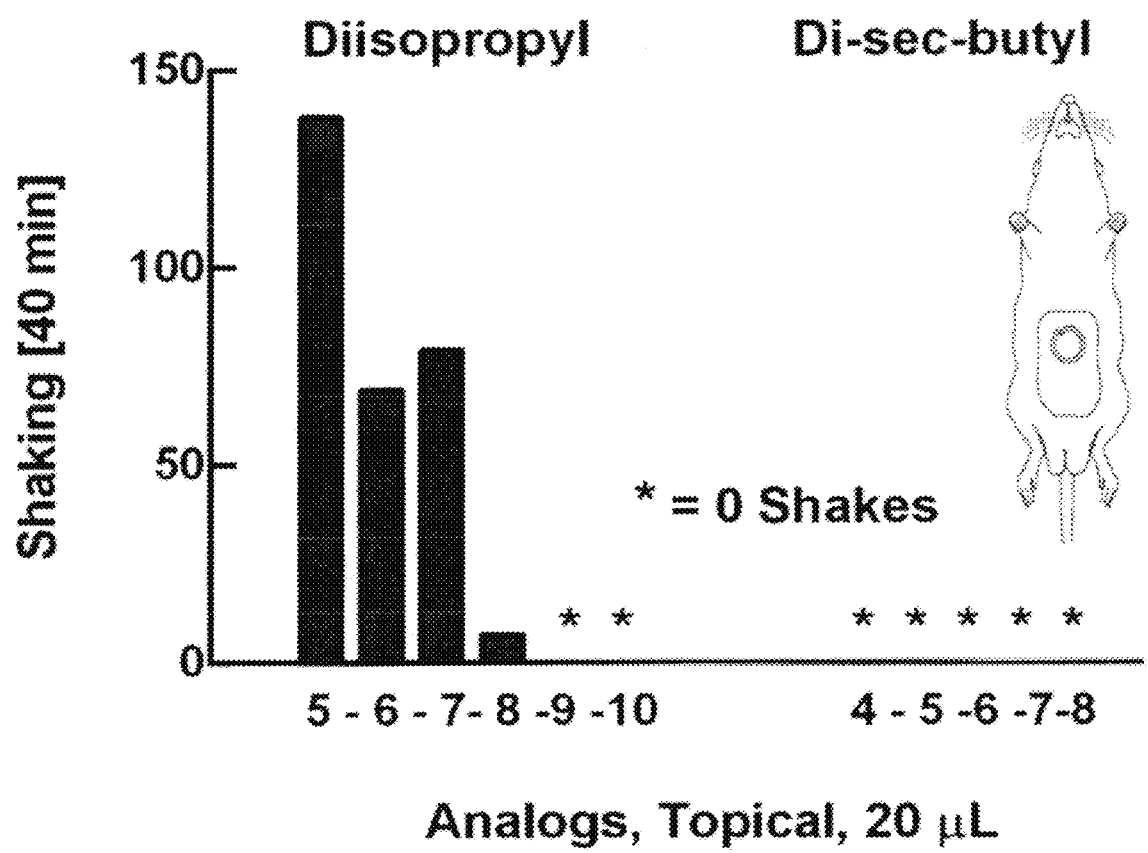
FIG. 6. shows the method for estimating the in vivo transdermal activity of the DIPA-embodiment compounds applied 20 μL with a micropipette to the center of a circle enclosed by cream on abdominal skin of an anesthetized rat. Shaking frequency was counted for 40 min after topical application. It can be seen that the embodiments DIPA-1-5, DIPA-1-6, and DIPA-1-7 evoke robust shaking, but this is not seen with other analogs.

FIG. 6 shows the method for measuring the transdermal activity of DIPA-compounds applied 20 µL with a micropipette to the center of a circle enclosed by cream on the abdominal skin of an anesthetized rat. Shaking frequency was counted for 1 hr after topical application. The data and results for topical for perioral responses are summarized in the Table 10. The data are further plotted graphically in FIG. 6, to show the lack of correlation of TRPM8 potency to in vivo bioactivity.

The data in Table 10 and FIG. 6 provide the STRONGEST evidence for the novelty and exceptional properties for the compounds of this discovery. It is clear that these compounds penetrate biological membranes and rapidly evoke responses; events that are not seen with the comparative di-sec-butyl analogs. Furthermore, the bioactivity is not correlated to the potency measurement [$EC_{50}$] on the TRPM8 receptor. This is the first time that shaking responses of such magnitude have been shown after topical [dermal] application of a chemical.

TABLE 10

Shaking frequency after perioral [per 20 mg/kg body weight] or topical delivery of 20 µl test compounds [per animal] to the anesthetized rat.

| Code | Mol Wt | # Cs | Sensation | Perioral | Topical | xMenthol |
|---|---|---|---|---|---|---|
| DIPA-1-5 | 204 | 11 | dynamic cool | 86 ± 7 | 138 ± 15 | 0.7 |
| DIPA-1-6 | 218 | 12 | dynamic cool | 56 ± 5 | 69 ± 8 | 1.6 |
| DIPA-1-7 | 232 | 13 | dynamic cool | 36 ± 4 | 79 ± 8 | 5.4 |
| DIPA-1-8 | 246 | 14 | cool | 0 | 7 ± 2 | 5.4 |
| DIPA-1-9 | 260 | 15 | mild cool | 0 | 0 | 4.0 |
| 2-4 | 218 | 12 | cool | 0 | 0 | 0.3 |
| 2-5 | 232 | 13 | cool | 4 ± 1 | 0 | 2.2 |
| 2-6 | 246 | 14 | cool | 0 | 0 | 4.7 |
| 2-7 | 260 | 15 | cool | 0 | 0 | 3.4 |
| 2-8 | 274 | 16 | cool | 0 | 0 | 2.9 |

Surprisingly, vigorous shaking was evoked with inventive embodiments DIPA-1-5, DIPA-1-6, and DIPA-1-7. Only a weak response was seen with DIPA-1-8, and the comparative di-sec-butyl analogs, 2-5, 2-6, and 2-7, were inactive. The shaking induced by DIPA-1-7 was dose-dependent. Topical application of 5 µl, 10 µl, 20 µl, or 50 µl of DIPA-1-7 elicited an average of 25±3, 53±6, 79±8 and 118±12 shakes, respectively, in 1 hr. Shaking was seen if DIPA-1-7 was diluted 50-50 with either water or saline (at the 10 µl dose), but it was completely inhibited if 50% (R)-1,2-propanediol was added to the DIPA-1-7 (at the 10 µl dose) as a diluent. This surprising result shows that DIPA-1-7 penetrates the skin in aqueous solution and is retarded by an alcoholic solvent. This facile permeability of DIPA-1-7 is reminiscent of menthol, and suggests DIPA-1-7 is easily delivered into the dermis by topical application. Furthermore, DIPA-1-7 may be used to penetrate thick keratotic skin lesions, for example in psoriasis or in contact dermatitis of the hands, to alleviate itch and pain. The adjustment of DIPA-1-7 concentrations in polyhydric solvent such as 1,2-propanediol can be used to control the degree of absorption of DIPA-1-7, an art well-known to formulation experts.

The surprising potency of DIPA-1-5 and DIPA-1-6 was unexpected. These molecules work for a shorter time on skin cooling than DIPA1-7. These smaller molecules may penetrate faster through the skin barrier and go into the systemic circulation. However, the value of this fast action is uncertain. In most contemplated topical applications of this discovery, the preference is for the drug action to remain localized and not systemic.

When the relative activities of the analogs for producing shaking are compared to the $EC_{50}$ for TRPM8 activation, it can be seen that the two variables are not correlated. The limitations of the TRPM8 $EC_{50}$ for predicting bioactivity were discussed on page.

The results here provide the strongest objective laboratory evidence that the DIPA compounds of Formula 1 selectively produce vigorous "dynamic cool". The total number of carbons, or the number of carbons in the largest alkyl group, did not correlate to the magnitude of bioactivity. The key factor to penetration was to avoid masking the phosphine oxide group with a butyl instead of a propyl group.

Study 7

Water Solubility and Penetration to Target

The receptor targets on the nerve endings are embedded in the epithelial cell layers. The epidermis is only ~1 mm thick, but a number of dead cell layers (stratum corneum), of denatured proteins impede access of the agonist molecule to the nerve endings. The heel of the feet is the thickest barrier, 86 cell layers for the heel, and followed by the palm of the hand, then the back of the hand. If you put an ice cube on the heel, you feel a bit of cold: but you will jump when you put it on the sole of the feet which has fewer layers. Unless the skin of these surface are structurally damaged, e.g. by inflammation, applying a cooling agent will not work, because the molecules do not access the nerve endings. For other surfaces, the genital skin (glans of the penis and vulva) and the eyelids are the thinnest, with 4 to 8 cell layers. The extremities, arms and legs, and the trunk (back) have thicker surfaces. The scalp is intermediate. The face varies: the cheek is relatively insensitive, but areas around cheekbone and nasolabial folds are thin and sensitive. These differences are important for drug action! For itching of the flexures of the limbs, e.g. elbow and knees, you need good drug penetration. For the eyelids and genital skin, you must choose your molecule carefully to get the desired effects: avoid too much stimulation and exert gentle cooling.

By contrast to the compounds tested by '496, applicant's preferred embodiments of DIPA-1-7, DIPA-1-8, and DIPA-1-9, wherein two of the alkyl groups (e.g. $R_2$ and $R_3$) are both isopropyl, have high water solubility and skin penetration. Increasing water solubility to increase bioactivity is counterintuitive in standard drug design for enhancement of transdermal drug permeation. Normally, formulation experts try to break down the stratum corneum with enhancers and chemists try to increase lipid solubility of the molecule (e.g. M. Prausnitz et al. Skin barrier and transdermal drug delivery. Chpt. 124, Medical Therapy, 2012). Nevertheless, the strategy used here was met with clinical success.

For the equivalent number of total carbons and hence equal molecular weights, applicant find that Dipa are at least 2 to 3× more water soluble than Dapa. In the Dipa series the polar phosphine oxide is not masked by the extra branched chain carbons. The Dipa are more hydrophilic than Dapa. Studies of skin permeation in vitro on hairless mouse skin confirmed the unusual penetrating power of the Dipa structure. In in vivo laboratory animals the pharmacological differences of the Dipa from Dapa congeners were strikingly different. Both Dipa and Dapa were active by intravenous injection, but only Dipa was active by or topical or oral routes of administration, indicating penetration across the dermal and gastrointestinal membranes of the Dipa, but not Dapa structures.

Figure 7:
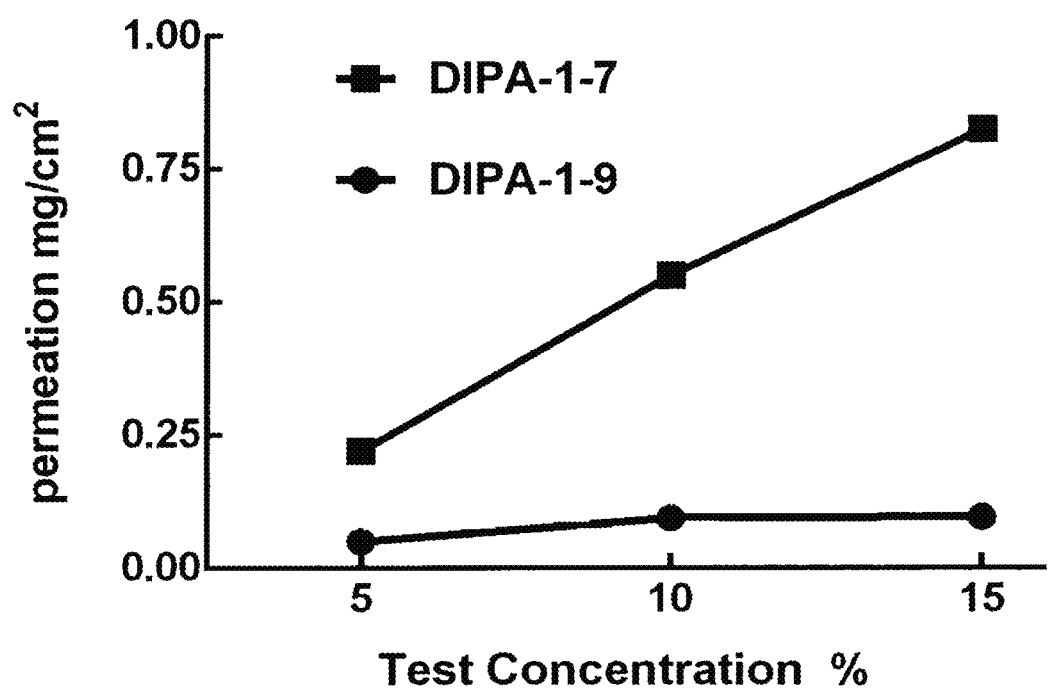
FIG. 7. shows the flux of DIPA-1-7 and DIPA-1-9 through excised hairless mouse skin in vitro. Test chemicals dissolved in a gel were placed in an incubation for 8 hr and the permeated amount of the chemical measured by a high pressure liquid chromatograph equipped with a refractive detector. These tests were conducted by Prof Choi of Chosun University, Korea. The flux of 1-7 was ~5× greater than 1-9. Standard enhancers with polyhydric alcohols, such as a propylene glycol-oleyl alcohol mixture (50:50) or Lauroglycol 90, designed to increase permeation added to the 1-7 gel decreased the rate of permeation by ~50%, indicating the importance of water solubility for permeation.

To further study the skin permeation of DIPA compounds, tests were conducted on the flux of DIPA-1-7 and DIPA-1-9 through excised hairless mouse skin in vitro (FIG. 7).

FIG. 7. shows the flux of DIPA-1-7 and DIPA-1-9 through excised hairless mouse skin in vitro. Test chemicals dissolved in a gel were placed in an incubation for 8 hr and the permeated amount of the chemical measured by a high pressure liquid chromatograph equipped with a refractive detector. These tests were conducted by Prof Choi of Chosun University, Korea. The flux of 1-7 was ~5× greater than 1-9. Standard enhancers with polyhydric alcohols, such as a propylene glycol-oleyl alcohol mixture (50:50) or Lauroglycol 90, designed to increase permeation added to the 1-7 gel decreased the rate of permeation by ~50%, indicating the importance of water solubility for permeation.

Standard enhancers with polyhydric alcohols, such as a propylene glycol-oleyl alcohol mixture (50:50) or Lauroglycol 90, designed to increase permeation added to the 1-7 gel DECREASED the rate of permeation by ~50%, indicating the importance of water solubility for permeation. In studies on the abdominal skin of anesthetized rat, it was found that a 50:50 propylene glycol-DIPA-1-7 mixture was inactive when tested on the skin of animals, with shaking as an endpoint, whereas the pure DIPA-1-7 was very active. Thus, normal solvents or enhancers of dermatological molecules impede rather than facilitate passage of the DIPA through the skin barriers.

The mobility of the DIPA molecules in an aqueous environment through a skin barrier is unusual and surprising. Apparently, if the polar "head" is masked by one or more carbon (e.g. methyl) groups, water solubility and permeability decrease. Alternatively, the symmetrical (achiral) arms (the isopropyl groups) may enable an efficient swimming of the DIPA through the pores of the stratum corneum and into the extracellular fluid, until the TRPM8 receptors in the stratum basale are reached. The DIPA configuration may be viewed as a "sperm" like head (the oxygen cloud about the phosphorus atom) that permits a polar interaction with water. The "swimming" motion may be impaired if the branched arms are asymmetrical (chiral).

Study 7

Effects on Topical Sites on the Cranium

DIPA-1-7, the most potent compound for dynamic cooling, was tested at other topical sites on the cranium. A 20 mg/mL solution was applied, using a cotton wipe, onto the skin above the buccal cheek, the parotid-masseteric cheek, temple, and the skin above the periauricular region, and the posterior mandible using the appropriate craniometric points (pterion, coronion, condylion, and gonion, respectively) as landmarks. Surprisingly, at all of these sites, other than the buccal cheek, little cooling, if any, was observed. Mild cooling was observed on the buccal cheek for approximately 30 minutes, but this effect may have been due to the spread of the solution onto the receptive field of the infraorbital nerve. It should be noted, however, the sensory effects of topical application of DIPA-1-7 may be influenced by inflammatory lesions that can alter permeability, for example, acne or acneiform lesions on the skin of the cheek.

The head is known to be a site where cooling helps relieve heat discomfort. In a study described in Nakamura et al. [2012], eleven male subjects were exposed to mild heat. Subjects, clothed in only short pants, entered a climatic chamber maintained at 32.5±0.5° C. with a relative humidity of 50%. About 1.5 hours after entry into the chamber, a local cooling protocol was initiated with water-perfused stimulators placed on the head, chest, abdomen, or thigh. Cooling of the face and thigh was felt by the subjects to be more effective than cooling of the chest and abdomen in reducing the heat discomfort.

In a study described by Essick et al. [Site-dependent and subject-related variations in perioral thermal sensitivity. Somatosensory & motor research 21, 159-75, 2004] the thresholds for detection of cooling and cold pain on various sites of the face, ventral forearm, and scalp was determined for 34 young adults. The most sensitive sites were on the vermilion which could detect a temperature change of about 0.5° C., followed by areas around the mouth (upper and lower hairy lip, mouth corner) and lateral chin. The midcheek and periauricular skin were less sensitive (able to detect a temperature change of about 2° C.), and the forearm and scalp were least sensitive (able to detect a temperature change of about 3° C.). The sensitivities of the orbital, zygomatic and forehead skin were not tested.

Use of DIPA-1-7 on the orbital and zygomatic/forehead skin, for example, in an office environment or in heat stress, may be inconvenient if the subjects uses cosmetic make-up at these sites. Surprisingly, it was found that DIPA-1-7, at 20 mg/mL, can produce a dynamic cooling effect when applied on the scalp, especially near the hairline. This effect is sufficient to counter fatigue caused by heat. Likewise, rubbing DIPA-1-7 on the skin in the centre of the chest, above the sternum, can counteract the discomforts of heat. At these application sites, cosmetics are not affected, yet an invigorating coolness, that counteracts the debilitating effect of heat, is achieved.

The ability of DIPA-1-7 to cause cooling of the scalp and hairline is also important for treating itch at these sites in conditions such as psoriasis, dandruff, and seborrheic dermatitis.

Case Studies

Case studies are described below which demonstrate the use of DIPA compounds in dermatological disorders and other conditions: (a) to counteract skin itch and pain in subject experiencing these dermatological symptoms (b) to break the "itch-scratch" cycle in a patient with atopic dermatitis, (c) to reduce the symptoms of urticaria, (d) to reduce the symptoms of cholestatic itch in a patient with liver disease, (e) to attenuate the discomfort of eyelid inflammation, (f) reduce the severity of "night sweats", and (g) to counteract the discomfort from heat stress (h) to treat the discomfort of genital inflammation. For several of these conditions, including urticaria and cholestatic itch, the surprise was the DIPA compounds were effective even when the keratinized skin is "intact", i.e. the stratum corneum is normal, and one would not expect a topical medication to penetrate and to be active.

In these studies, subjects were given dosages units containing 1.5 to 1.75 mL of DIPA-1-7 stored in 2.0 mL microcentrifuge tubes (Nova Biostorage Plus, Canonsburg, PA 15317) and cotton gauze (0.4 g, rectangular, 50 mm×60 mml; from CS-being, Daisan Cotton, Japan). The DIPA-1-7 was provided as a solution in distilled water, at a DIPA-1-7 concentration of 5 mg/mL to 20 mg/mL. The subjects were given instructions on how to place wet the gauze and how to wipe over the skin. Approximately 0.15 mL to 0.35 mL per unit wipe were delivered by these methods of application. Subjects were instructed to rinse with water if any surface become irritable; however, irritation and discomfort were not seen with DIPA-1-7, DIPA-1-8, or DIPA-1-9 at the test concentrations.

Case Study 1

Contact dermatitis. Two scientists working in the laboratory had allergic dermatitis of the hand in response to detergents and soaps. The hands were inflamed and extremely itchy. Applications of DIPA-1-7, 20 mg/mL, with a cotton-tipped applicator or gauze immediately stopped the itch and this effect lasted for at least 2 hours, and the suppression could be renewed by repeated application. One scientist, a world-renowned dermatologist with many publications on itch, noted that the DIPA-1-7 produced an "icy-cool" feeling on the inflamed skin and he had never encountered such a compound that was so effective in stopping itch so quickly.

A pharmacologist liked to work in the garden, but the thorns from bougainvillea stems and rose bushes, and the hair from azalea leaves, irritated his skin and caused intense itch. He noted that the sensory discomfort on the skin could be instantly stopped by DIPA-1-6 or DIPA-1-7, applied either as a 20 mg/mL aqueous solution, or as a cream (mixed with Eucerin Moisturizing Cream). These effects could also be obtained with DIPA-1-8. He also noted that the irritation and itch caused by insect bites could be immediately stopped by these agents.

Case Study 2

Atopic dermatitis A 8-year old boy had atopic dermatitis since childhood and exhibited the standard scars on the flexures of his elbow and knees. He had been treated with topical steroids, but the skin had become thin and easily broken. He objected to topical ointments because of the excessive "greasy" feel and stickiness, and because he felt they were not effective in stopping the itch. He also used moisturizers. The itch interfered with his sleep, especially during periods when his allergic rhinitis flared up. His parents were concerned with the scratching at night, poor scholastic performance, and lack of concentration. The subject was given 8×8 cm wipes saturated with 2 mL of DIPA-1-7 at 10 mg/mL in water, and given instructions to use the wipes after washing, to wipe over skin sites that itched in the evening, as he prepared for sleep. The wipes were immediately effective in reducing itch and scratching and facilitated sleep. Over a 2-week period of use, the skin lesions became less red, formed scabs, and progressed to heal. It was clear that the itch-scratch cycle had been attenuated. The boy became more cheerful and he paid more attention to his schoolwork. His parents were extremely pleased.

Case Study 3

Pruritis and Xerosis of the Elderly An eighty-six year old retired widower decided to move from California to a hotel suite in Hong Kong for permanent residence. He had been an avid and skilled golfer for many years and had actinic keratosis and a dry skin. Over time, his skin became itchy, especially on the forearms and back torso. Scratching with a wooden stick on his back at first helped, but the skin became damaged, infected, and inflamed. He applied Eucerin's "Atopic Control" which helped relieve the dryness, but found it to be expensive, heavy and "greasy", although it definitely provided some protection and relief. The itching and inflamed skin became unbearable during the hot summer months in Hong Kong, when the air conditioning was on full blast, and during the dryness of the fall season. His dermatologist prescribed a potent topical steroid, but his skin became fragile, infected, and ulcerated in some areas. His life was miserable because of the skin discomfort. He agreed to try a DIPA-1-8 solution, 10 mg/mL in isotonic saline. He applied about 20 drops of the DIPA-1-8 onto a 8×8 cm wipe made of 100% viscose 50 grams per square meter. After wiping, the volume off-loaded onto his skin was about 0.2 to 0.25 mL, so the total dose per wiping was 2 to 2.5 mg. The topical application of the DIPA-1-8 relieved his itch within 3 to 5 min after wiping, and he stopped complaining of skin discomfort. He said the wipes when applied to the face, also gave the sensation of wetness, and thus may be useful for cosmetic applications. He continued the use of the wipes on an as need basis and his skin, formed scabs, healed, and resumed a normal appearance. His only negative comment was that the solution made him feel too cool when the air conditioning was on a high setting. He continued using the wipes until death from a bulbar stroke three years later.

Case Study 4

Urticaria Urticaria (hives) is an allergic condition in humans manifested by skin rashes (wheals). The symptoms of redness, swelling, and itch on the skin are caused primarily by release of histamine from mast cells into the dermal layers. A frequent trigger for hives is the ingestion of seafood. Here is a description of a case of urticaria treated with DIPA-1-7, formulated 1.5% wt/vol in a gel made by Dong Wha Pharmaceuticals (Seoul, Korea). A female subject with a history of hives went to a seaside resort in the South of France and consumed over two days seafood pasta, minced crab, and mixed seafood soups. She developed extensive welts on her buttocks with the classic signs of inflammation, namely, "calor" (heat on touch of the inflamed tissues), "rubor" (redness caused by vasodilatation), "tumor" (swelling) and "dolor" (pain and itch). Wheals also appeared on the skin above the clavicle and on her neck. It was distressing. Application of the gel on the skin diminished all four signs of inflammation beginning about 5 to 10 min after application. The subject described the effect as "burning cold" and then robust cool, but excellent for decreasing the sense of itch and "heat" from the red welts. Swelling, redness, and "flare" were visibly diminished 30 min after application. The gel was applied again 3.5 hr later, and then the subject given three tablets of fexofenadine (120 mg) and a tablet of chlorphenhydramine (4 mg). All the signs and symptoms of the hives were viewed as being diminished by at least 50% and "under the control" by the subject in 12 hr, and the skin rashes disappeared after three days and did not recur.

This is the first report in which the skin dysesthesia (itch and a sense of heat) and other signs of inflammation caused by urticaria are reduced rapidly after topical medication (1.5% DIPA-1-7 in a gel). The rapid effectiveness of DIPA-1-7 applied to the relatively thick skin of the buttocks (15 to 18 cell layers of stratum corneum) indicated permeation to the nerve endings that allowed the symptoms and signs of inflammation to be alleviated. The therapeutic effect and rapid onset is of sufficient intensity to benefit the patient.

Additional case studies with DIPA-1-7 gel in 8 cases of urticarial dermatoses were obtained by an established dermatologist in a leading hospital in Seoul, Korea. The satisfactory suppression of itch was obtained in 75% of patients. In this study, there were also 5 cases of atopic dermatitis, 6 cases of seborrheic dermatitis, 3 cases of prurigo nodularis, and 3 cases of herpes zoster. In the cases tested, the skin dysesthesia intensity was assessed on a visual analog scale after use of DIPA-1-7 for one week. It was clear that the DIPA-1-7 gel had benefits in a variety of dermatological disorders.

Case Study 5

Cholestatic Itch A 80-year renowned Professor of History was diagnosed with terminal liver cirrhosis. His children learned of the anti-itch medication and requested samples because he was constantly itching and scratching. At first, the condition was incorrectly called eczema, but upon examination the skin was in fact intact. The subject was suffering from cholestatic itch. The subject was given cotton gauze squares and 30 mL plastic dropper bottles containing 2% DIPA-1-7 in water. He was instructed to wet the squares and wipe the solution on the site of itch on an as needed basis. The subject declared after his first trial that this was the best medication he had ever tried for the itch and that it worked. He used about one 30 mL bottle every three days and demanded more. This regimen continued until the subject expired three months later.

Case Study 6

A 28-year old female subject visited her optometrist with the typical complaints of dry eye disease disorder, namely, a sense of discomfort from the eye surface, blurring of vision, sensitivity to light, and problems with reading, driving, and using the smartphone screen. Upon examination, she was found to have hyperemia of the eyelid margins, blockage of the Meibomian gland ducts, some thickening of the eyelid Further questioning revealed that she was using a bimatoprost solution to induce hypertrichosis, but was applying the solution two or three times of a day (instead of the suggested single application per day) because she was dissatisfied with the slow rate of eyelash growth.

She was instructed not to use eye makeup and given Blephaclean™ eye wipes, which are single unit wipes with a cleansing solution, to clear the Meibomian gland ducts and to maintain eye hygiene. The subject, however, objected vehemently to the irritation caused by the cleansing wipes and her inability to continue use of the bimatoprost solution, which was quite expensive. The subject was recruited into a clinical trial of a DIPA-1-9 wipe, 2 mg/mL in water, and instructed to use the wipe once in the morning, once in the evening, and two more wipes on an as needed basis during the day. She felt immediately better upon using the DIPA-1-9 wipes and commented on the cooling and refreshing sensations that were now present on her ocular surface and margins. She said her bimatoprost solution now no longer irritated and her eyelashes were now thick and luxurious. She recommended that the DIPA-1-9 be added to the bimatoprost solution as an adjunct. She offered to pay for a continued supply of the DIPA-1-9 wipes.

Case Study 7

Heat stress In a series of studies, a towelette was used for delivery instead of a wipe. The towelette consisted of a plastic wrap (weight 1.1 g), a 23 cm×26 cm towel of non-woven lace (weight 3.4 to 3.5 g) and a liquid composition (14 to 15 mL) which was automatically added to and sealed off in the wrapper. Automated machinery for producing towelettes are well-known to the art. Here, the towelettes were produced by Kank Factor, LLC, San Francisco (721 Commercial Street, San Francisco CA 94108, www.3LWipes.com). These towelettes were then further treated to form either embodiments for practicing the present invention or as placebo controls, as follows. Distilled water (as placebo controls) or DIPA-1-7 dissolved in distilled water (at a concentration of 1 to 5 mg/mL) was incorporated into the towelette. The volume per self-application depended on the application site, but was about 0.3 mL to 0.5 mL for the face and brow, but could be higher if wiping of the torso was also included.

The towelettes were stored in a refrigerator but then stored at room temperature for at least 1 hour before use. Effective sterilization of the towelette could be obtained by placement in a microwave oven for 1 min [Tanaka, Y. et al. Warming and sterilizing towels by microwave irradiation. Yonago Acta Medica 41: 83-88, 1998]. Subjects were instructed to hold the towelette with both hands, and bring the towelette against the face, like how one would use a small wet face towel, and to keep the eyes closed. The skin of the face is moistened and medicated by this procedure. Once the subject has learned what to expect, the subject can adjust the dosage (e.g., by dabbing), as needed, to achieve the desired anti-fatigue/anti-heat effects. After one or two trials, individuals quickly learn how to apply the sensory agent without any risks of discomfort.

During an "Indian Summer" heat wave in the San Francisco Bay Area, the outside temperature was 30 to 33° C. with a cloudless sky and an intense bright sun. The towelette, described above, was used as a substrate to deliver DIPA-1-7 to the skin of the chest and armpits of several individuals who complained vigorously about heat stress and discomfort. Comfortable cooling was noted for more than 3.5 hours with decreased sweating. These Individuals were able to work normally in the heat in an office environment without need for additional cooling.

A 70-year old from Northern California went on a 7-day golf vacation to Las Vegas in September. He played at least one round of golf each day and sometimes two. He did not wear a hat or use sunscreen. On the third day of vacation, the subject showed the classic signs and symptoms of sunburn: redness and flushing of the facial skin, a sense of persistent warmth, pain, and tenderness of the face, a mild degree of swelling around the eyes, and a throbbing headache. He volunteered to try a cream containing 1% wt/vol DIPA-1-8 and wiped about 0.5 mL of the cream over his cheeks and cheekbone. Surprisingly, he noted an immediate relief of skin discomfort which lasted for at least four hours. His headache was gone, and he said his face felt "comfortable and normal". He used the cream on an "as needed" basis and reduced his exposure to direct sunlight by wearing a wide-brimmed hat and applying copious amounts of sunscreen products. He said that the cream would be especially useful for the dry hot climates of Los Angeles, Phoenix and other parts of Arizona, and for Texas, and for countries such as Australia and the Middle East, because it also relieved the sense of dryness on the face and gave a feeling of "wetness" after repeated use. This relief of "post-sunburn" pain, burning, redness, and discomfort was confirmed in ten other cases.

Case Study 8

Lichen sclerosus atrophicus A 40-year old suffered from penile lichen sclerosus. This is an inflammatory dermatosis of the glans penis and foreskin and, in this particular case, was associated with intense pruritus and dysesthesias (burning sensations). The patient, under the supervision and care of his dermatologist, volunteered to try DIPA-1-8 on his lesion and he was supplied with various concentrations of DIPA-1-8 dissolved in distilled water. After self-experiment, he concluded that concentrations of 1 to 1.5 mg/mL of DIPA-1-8 produced significant relief, but a concentration of 2 mg/mL of DIPA-1-8 was too cold and uncomfortable. The solutions were applied with cotton-tipped applicators or gauze wipes. The advantage of using DIPA formulations for genital skin is water solubility. This minimizes the need for excipients and the likelihood of further irritation. The subject suggested that an aerosolized spray may also be a convenient method of drug delivery.

These studies illustrate the anti-nociceptive properties of DIPA-1-7 and DIPA-1-8, especially on itching. DIPA-1-8 had a longer duration of action than DIPA-1-7, and may be the preferred agent for dermatological applications. Further studies showed that DIPA-1-9 at 2 mg/mL applied with with a wipe on the glans or on the vulva produced that a gentle cooling and refreshing sensation that counteracted any inflammatory discomfort.

Case Study 9

Three subjects decided to systemically compare DIPA-1-6, DIPA-1-7, DIPA-1-8, and DIPA-1-9 for their sensory effects on the ocular surface. Each compound was prepared at 1 mg/mL in distilled water. A cotton tipped applicator of a specific size (Puritan 803-PCL) consisting of a 55 to 75 mg ball of cotton wound around the tip of a three inch polystyrene rod was dipped into the solution. The tip was then applied, with the eyelids closed, to the lower aspect of the upper eyelid, onto the eyelashes, with two lateral to medial wiping motions. The subjects were then instructed to blink. By blinking, the solution is then evenly distributed over the pre-corneal film. This "swab" delivery method off-loaded a total of ~35 μL of liquid onto the surface of both eyes. DIPA-1-6 caused significant stinging and discomfort and was therefore not further studied. DIPA-1-7 and DIPA-1-8 produced strong and refreshing cooling, which counteracted eye irritation, and increased cognitive functions. For example, subjects felt they could focus on distant objects and enjoy the view. They felt mentally alert and refreshed. But, with both DIPA-1-7 and DIPA-1-8, there was a small residue left on the eyelid; subsequently using a towel to wash the face can cause eye irritation. Surprisingly, DIPA-1-9 did not produce any eye irritation when wiped over the eyelid, nor did it leave a residue. It also produced refreshing cooling, but not with the same intensity as DIPA-1-7 or DIPA-1-8. On the other hand, DIPA-1-9 has ideal properties for the treatment of ocular discomfort, e.g., discomfort caused by eye strain; eye fatigue; eye surgery; an airborne irritant or pollutant that interacts with the eye surface; extended wear of contact lenses; excessive exposure to the sun; conjunctivitis; or the dry eyes syndrome.

Summary of Observations

The structures of Rowsell and Spring '496 were described 40+ years ago, but were not developed for use. The applicant found that diisopropyl analogs were not described in '496. He then synthesized and tested these analogs. The "head" of the prototypical DIPA molecule is polar (hydrophilic) and soluble in the polar environment of water. This increased water-solubility of the analogs facilitates permeation past dead cell layers of the stratum corneum to access skin nerve endings. The preferred embodiments, 1-7 and 1-8 exert a robust cold sensation that can modulate skin dysesthesia caused, for example, by various dermatitis (e.g. atopic or urticaria) and by dryness (xerosis). The '496 structures have their "head" covered by more lipophilic groups and are chiral, and are less able to permeate to target receptors in the basal layers of the skin to achieve the same therapeutic endpoints as the preferred embodiments. Increasing water solubility is counterintuitive in standard drug design for enhancement of transdermal drug permeation. Normally, formulation experts try to break down the stratum corneum with enhancers and chemists try to increase lipid solubility of the molecule (e.g. M. Prausnitz et al. Skin barrier and transdermal drug delivery. Chpt. 124, Medical Therapy, 2012). Nevertheless, the strategy used here was met with clinical success. Thus, the applicant opines that the discovery of the DIPA embodiments is not obvious and is a quantum improvement in the discovery process.

For the equivalent number of total carbons and hence equal molecular weights, applicant find that DIPA are about 10× more water soluble. Studies of skin permeation in vitro on hairless mouse skin confirmed the penetrating power of the DIPA. In in vivo laboratory animals the pharmacological differences of the DIPA from the mixed isopropyl/sec-butyl and di-sec-butyl congeners were strikingly different. Both DIPA and di-sec-butyl were active by intravenous injection, but only DIPA was active by or topical or oral routes of administration, indicating better penetration across the dermal and gastrointestinal membranes of the DIPA, but not di-sec-butyl structures. The ability of the DIPA structures to relieve skin discomfort in patients with an intact stratum corneum and a dermatological disorder was rapid, dramatic, and unexpected.

REFERENCES

A number of publications are cited herein in order to more fully describe and disclose the discovery and the state of the art to which the discovery pertains. Each of these publications is incorporated herein by reference in its entirety into the present disclosure

The invention claimed is:

1. A therapeutic method for the treatment of itch caused by a skin dysesthesia in a subject in need of treatment thereof, comprising:
    topically applying a semi-liquid composition to keratinized tissues of the subject's skin, the composition comprising a therapeutically effective amount of one or more compound having Formula 1

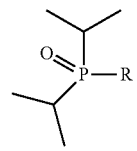

Formula 1 wherein R is n-heptyl, n-octyl or n-nonyl;

and wherein the composition, following topical application, penetrates the keratinized tissues of the subject's skin.

2. The method as in claim 1 wherein the composition has from about 0.05 to 2% by weight of the Formula 1 compound.

3. The method as in claim 1 wherein the Formula 1 compound is 1-diisopropyl-phosphinoyl-heptane (DIPA-1-7), 1-diisopropyl-phosphinoyl-octane (DIPA-1-8) or 1-diisopropyl-phosphinoyl-nonane (DIPA-1-9) and the therapeutically effective amount is from about 1 to 20 mg/ml.

4. A method for the treatment of dermatitis in a subject in need of treatment thereof, the method comprising:
    topically applying a liquid or semi-liquid composition to keratinized tissues of the subject's skin, the composition having comprising a therapeutically effective amount of one or more compounds having Formula 1

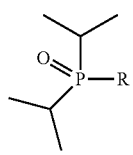

Formula 1 wherein R is n-heptyl, n-octyl or n-nonyl; and
wherein the liquid or semi-liquid composition, following topical application, penetrates the keratinized tissues of the subject's skin.

5. The method of claim 4 wherein the dermatitis is atopic dermatitis.

6. The method of claim 4 wherein the dermatitis is contact dermatitis.

7. The method of claim 4 wherein the liquid or semi-liquid composition has from about 0.05 to 2% by weight of the Formula 1 compound.

8. The method of claim 4 wherein the Formula 1 compound is 1-diisopropyl-phosphinoyl-heptane (DIPA-1-7), 1-diisopropyl-phosphinoyl-octane (DIPA-1-8), and/or 1-diisopropyl-phosphinoyl-nonane (DIPA-1-9), and the therapeutically effective amount is from 1-20 mg/ml.

9. A method for the treatment of pruritus in a subject in need of treatment thereof, the method comprising:
topically applying a liquid or semi-liquid composition to keratinized tissues of the subject's skin, the composition having comprising a therapeutically effective amount of one or more compounds having Formula 1

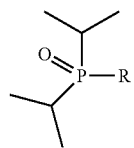

Formula 1 wherein R is n-heptyl, n-octyl or n-nonyl; and
wherein the liquid or semi-liquid composition, following topical application, penetrates the keratinized tissues of the subject's skin.

10. The method of claim 9 wherein the liquid or semi-liquid composition has from about 0.05 to 2% by weight of the Formula 1 compound.

11. The method of claim 9 wherein the Formula 1 compound is 1-diisopropyl-phosphinoyl-heptane (DIPA-1-7), 1-diisopropyl-phosphinoyl-octane (DIPA-1-8), and/or 1-diisopropyl-phosphinoyl-nonane (DIPA-1-9), and the therapeutically effective amount is from 1-20 mg/ml.

* * * * *